(12) United States Patent
Fichou et al.

(10) Patent No.: US 8,383,931 B2
(45) Date of Patent: Feb. 26, 2013

(54) DERIVATIVES OR DIPYRANNYLIDENE TYPE AS ANODE INTERFACE LAYER IN ELECTRONIC DEVICES

(75) Inventors: Denis Fichou, Paris (FR); Stéphane Berny, Orsay (FR); Ludovic Tortech, Gif sur Yvette (FR)

(73) Assignees: Commissariat a l'Energie Atomique, Paris (FR); Centre National de la Recherche Scientifique, Paris (FR); Universite Pierre et Marie Curie (Paris 6), Paris (FR)

( * ) Notice: Subject to any disclaimer, the term of this patent is extended or adjusted under 35 U.S.C. 154(b) by 565 days.

(21) Appl. No.: 12/577,945

(22) Filed: Oct. 13, 2009

(65) Prior Publication Data

US 2011/0083730 A1  Apr. 14, 2011

(51) Int. Cl.
*H01L 31/00* (2006.01)
(52) U.S. Cl. ... 136/256; 328/205; 357/40; 357/E51.041; 428/323; 438/82; 540/1; 549/13; 549/415
(58) Field of Classification Search ............... 136/256; 328/205; 357/40, E51.041; 428/323; 438/82; 540/1; 549/13, 415
See application file for complete search history.

(56) References Cited

U.S. PATENT DOCUMENTS 4,365,017 A * 12/1982 Detty et al. ............ 430/83
2009/0044855 A1* 2/2009 Irwin et al. ............ 136/255

FOREIGN PATENT DOCUMENTS

SU  609756  * 5/1978

OTHER PUBLICATIONS

Yamashita et al. (Chem. Mat. Comm. 2009, 21,4350-52, P/D:08/09).*

* cited by examiner

*Primary Examiner* — Shane Fang
(74) *Attorney, Agent, or Firm* — Alston & Bird LLP

(57) ABSTRACT

The present invention relates to substrates coated with films comprising compounds of general formula (I) below:

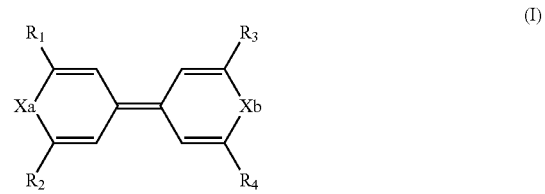

(I)

Figure 1:
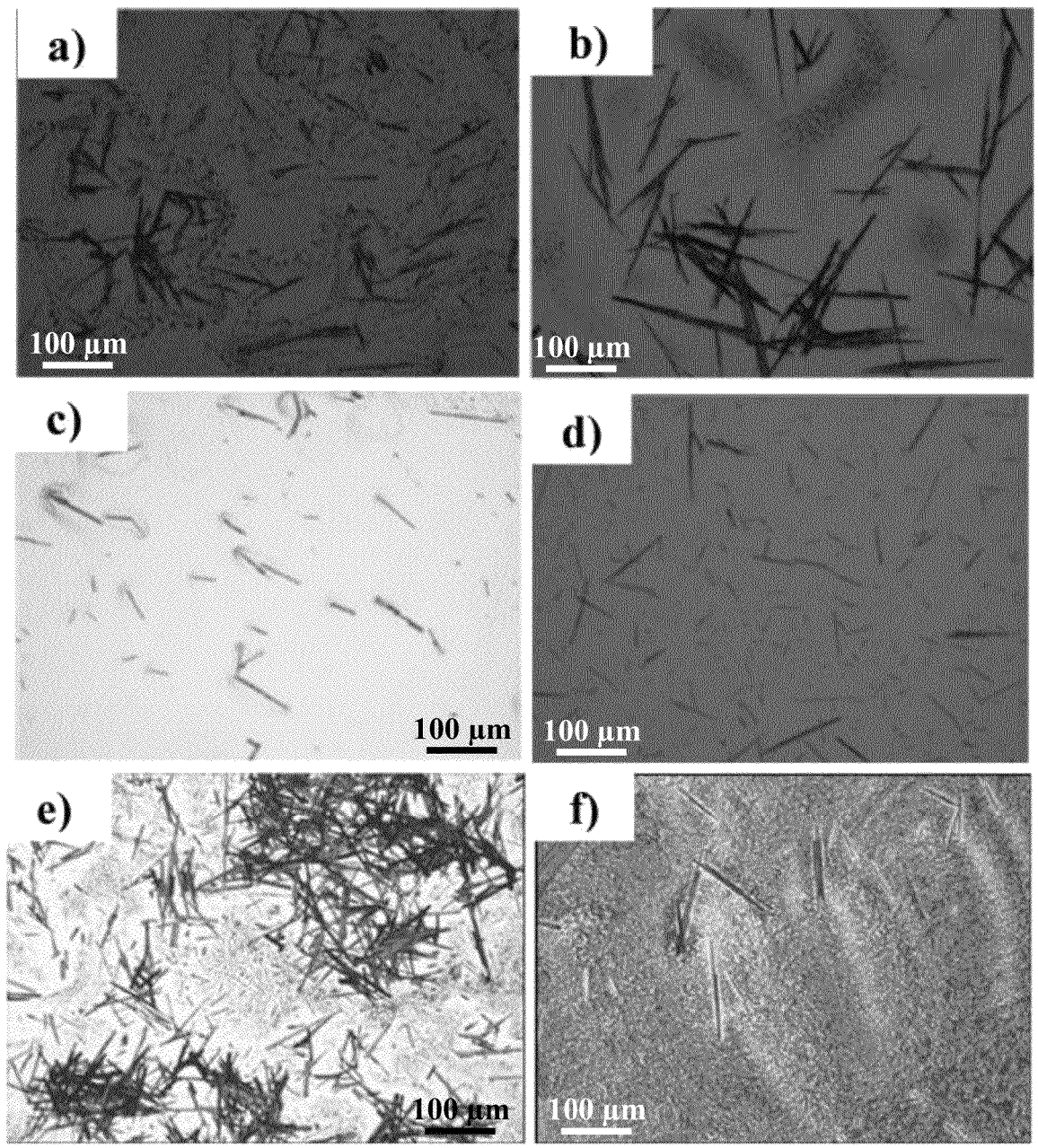

and also to the process for manufacturing them and to their use as anode interface layer in electronic devices.
The present invention also relates to organic electroluminescent diodes (OLED), polymeric electroluminescent diodes (PLED), organic field-effect transistors (OFET) and organic solar cells (OSC) comprising a substrate according to the invention, to specific organic solar cells and to the process for manufacturing them.
Compounds of formula (I) as such also form part of the invention.

20 Claims, 16 Drawing Sheets

DERIVATIVES OR DIPYRANNYLIDENE TYPE AS ANODE INTERFACE LAYER IN ELECTRONIC DEVICES

The present invention relates to substrates coated with films comprising compounds of formula (I), to the process for manufacturing them and to their use as anode interface layer in electronic devices. The present invention also relates to organic electroluminescent diodes (OLED), to polymeric electroluminescent diodes (PLED), to organic field-effect transistors (OFET) and to organic solar cells (OSC) comprising a substrate according to the invention, to specific organic solar cells, and to the process for manufacturing them. Finally, the present invention relates to compounds of formula (I) as such.

Current electronic systems such as OSCs require complex technologies that render the optimization of their optical and electronic performance difficult.

One of the main optimization routes consists in using at the anode of the photovoltaic system a conductive polymer such as poly(3,4-ethylenedioxythiophene)-poly(styrene sulfonate) (PEDOT:PSS), this polymer being inserted between a tin-doped indium oxide (ITO) electrode and a photosensitive active layer (Crispin et al., Journal of Polymer Science Part B: Polymer Physics, Vol. 41, 2561-2583 (2003)). Substrates coated with PEDOT:PSS are optically anisotropic and absorb little in the visible range; the conductivity of substrates coated with PEDOT:PSS prepared using commercial solutions is generally between 1 and 50 $S \cdot cm^{-1}$.

PEDOT:PSS-based devices are still currently the subject of numerous studies (Groenendaal et al., Adv. Mater., 2000, 12, No. 7) relating to:
- improving the photosensitive active layer by using novel absorbent materials, by structuring the charge network, or by improving the transportation of the charges, and
- improving the interfaces by means of better quality of contacts or charge collection.

Thus, the anode interface layers used in electronic devices must have:
- good electronic properties, and more particularly high conductivity, and also suitable output work making it possible to optimize the energy barrier at the interface between the ITO electrode and the photosensitive active layer, facilitating the collection of positive charges,
- good optical properties characterized by minimal absorption, and
- good stability and ease of forming, allowing the formation of continuous homogeneous films.

The term "output work" means the minimum energy, measured in electron-volts (eV), needed to strip an electron from the Fermi level of a metal to a point of infinity beyond the metal. The photoelectric effect consists of a release of an electron when a photon having an energy greater than the output work strikes the metal. The difference between the energy of the incident photon and the output work is given to the electron in the form of kinetic energy. Thus, the photoelectric output work is calculated according to the formula:

$$\phi = h \cdot f_0$$

in which h is Planck's constant and $f_0$ is the minimum photon frequency at and above which photoelectric emission takes place.

The output work of electrodes plays a crucial role in the field of plastic electronics since it has an influence on the distribution of the internal electric field and the height of the energy barrier between the electrode and the photosensitive active layer of the device. This barrier has a great influence on the injection of the charge carriers, especially in the case of OLEDs, or, on the contrary, dominates the collection of charges from the active layer to the electrode, for instance in the case of OSCs. In order to facilitate hole transportation, materials with high output work values are preferred as anode.

At the present time, the devices most commonly used are PEDOT:PSS-based devices. However, when it is used as an interface layer on ITO electrodes, the PEDOT:PSS must be applied in the form of a thin film less than a few hundred nanometers thick, in order to ensure high optical transmission; in this case, the PEDOT:PSS film has low conductivity. Surface defects and holes may also appear at the surface of the PEDOT:PSS film when the applied polymer layers are too thin. On the other hand, when it is applied as a thicker layer (between 150 and 200 nm thick), i.e. to achieve higher conductivities allowing lateral transport of the photocurrent, a loss of optical transmission coefficient is then observed.

PEDOT:PSS-based systems also have other drawbacks:
- the interface between the PEDOT:PSS films and ITO-based electrodes is unstable, since the indium atoms diffuse into the polymer layer and impair its efficiency,
- the electrical contact between the PEDOT:PSS films and ITO-based electrodes is poor, since the polymer film does not have access to many electronically active sites of the surface of the ITO electrode, which increases the series resistances and greatly reduces the collection of the holes at the electrode,
- the conductivity and roughness of the PEDOT:PSS layers are dependent on the application conditions, and in particular on the degree of humidity and the annealing temperatures.

Routes for substituting for the use of conductive polymers at the anode interface have also been envisioned, for instance:
- the use of monolayers (Campbell et al., Appl. Phys. Lett., 71 (24), 3528-3530; Kim et al., Appl. Phys. Lett., 92, 133307 (2008); Ackerman et al., Small 2008, 4, No. 1, 100-104; Armstrong et al., Thin Solid Films, 445, 2003, 342-352), the latter generally being bonded covalently via chemical or electrochemical means to the surface of the ITO electrode. However, these monolayers are relatively thin (a few tens of angströms) and lead to unequal coverage of the substrates they functionalize, leaving rough areas and thus leading to interfaces of mediocre quality,
- the use of charge-transfer complexes (Hanson et al., J. Am. Chem. Soc., Vol. 127, No. 28, 2005, 127, 10058-10062; Kahn et al., Appl. Phys. Lett., Vol. 79, No. 24, 4040-4042), the latter, however, having the drawback of having energy levels that are difficult to adjust.

Thus, the technical problem remaining to be solved with respect to this prior art consists in developing substrates coated with homogeneous thin films, the interface between the layers and said films needing to be of high quality and to have a high degree of the crystallinity, and thus more conduction pathways for the collection of positive electrical charges (holes), in comparison with those of the polymer films currently used, substrates coated with such films thus being able to be used in electronic devices such as hole-collecting layers, by virtue of a hole mobility that is greater than that of the films of the prior art, but also by virtue of energy levels that are intermediate between the anode electrode and the photosensitive organic layer.

The substrates of the invention propose to overcome the drawbacks of the current conductive polymers, by virtue of a compromise of performance qualities that are difficult to achieve and that more particularly satisfy the following needs and requirements:

- ease of use, allowing the formation of substrates coated with continuous homogeneous films on the anode electrode, by means of a high degree of coverage and good wettability of the photosensitive active layer, i.e. a good capacity to form a continuous homogeneous film on the photosensitive active layer, said films preferably being less than 45 nm thick,
- high hole mobility, i.e. an intrinsic capacity to conduct positive charges from the photosensitive active layer to the ITO electrode,
- a lowered energy barrier, the energy level of the film of the invention needing to be intermediate between those of the materials that surround it, promoting the collection of positive charges at the anode, and
- excellent optical properties, the films of the invention having a high transmission coefficient in the visible region, all these properties making it possible to increase the conversion yields of the electronic devices in which the substrates of the invention are used.

This objective is achieved by substrates coated with films comprising at least one compound of formula (I), as described hereinbelow, and which constitute the first subject of the invention. A subject of the present invention is also a process for manufacturing such substrates, and the use of these substrates as anode interface layer in electronic devices. Organic electroluminescent diodes (OLED), polymeric electroluminescent diodes (PLED), organic field-effect transistors (OFET) and organic solar cells (OSC) comprising a substrate according to the invention, and also specific organic solar cells and the process for manufacturing them, also form part of the invention. Lastly, a final subject of the invention concerns compounds of formula (I) as such.

Thus, a first subject of the present invention is a substrate coated with a film comprising at least one compound of formula (I) below:

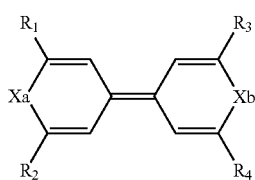

in which:
- Xa and Xb, which may be identical or different, are chosen from N, P, O, S, Se and Te atoms,
- $R_1$, $R_2$, $R_3$ and $R_4$, which may be identical or different, represent a group chosen from aryl and heteroaryl rings containing 4 to 10 carbon atoms, said aryl or heteroaryl rings possibly being substituted with one or more halogen atoms, hydroxyl groups —OH, alkyls containing 1 to 30 carbon atoms, alkoxy —OC$_n$H$_{2n+1}$ or ester —C(O)OC$_n$H$_{2n+1}$, in which $0 \leq n \leq 30$ and preferably $0 \leq n \leq 16$, the compound of formula (I) being present in said film in the form of particles with a mean diameter of less than or equal to 300 nm, preferably less than or equal to 250 nm and even more preferentially less than or equal to 200 nm.

The substrate of the invention may be an oxide-based substrate, such as tin-doped indium oxide (ITO), iron oxide, aluminum oxide or silicon oxide, coated with a film as defined above.

Said film consists of a matrix in which particles of the compound of formula (I) are substantially uniformly distributed, and constitutes a continuous material of measurable thickness. Said film preferably has a thickness of less than 45 nm, preferably less than or equal to 30 nm and even more preferentially less than or equal to 15 nm.

Electron-donating compounds such as the compounds of formula (I) of the invention have already been described in the prior art (Sandman et al., J. Chem. Soc., Chem. Commun., 1977, 687, 177-178; Otsubo et al., J. Chem. Soc. Perkin Trans., 1993, 1815-1824; Berenjian et al., Can. J. Chem., Vol. 59, 1981, 2612-2616), these compounds, however, not having been used to date for electronic applications such as those of the invention.

For the purposes of the present invention, the following definitions apply:

- Alkoxy: a group O-alkyl in which the alkyl group is a saturated, linear or branched hydrocarbon-based aliphatic group;
- Halogen atom: a bromine, chlorine, iodine or fluorine atom; bromine, chlorine and fluorine being preferred;
- Aryl group: denotes any functional group or substituent derived from at least one aromatic ring; an aromatic ring corresponds to any flat monocyclic or polycyclic group comprising a delocalized π system in which each atom of the ring comprises a p orbital, said p orbitals overlapping each other;
- Heteroaryl group: denotes any functional group or substituent derived from at least one aromatic ring as defined above and containing at least one heteroatom chosen from N, P, O and S.

According to one preferred embodiment of the invention, the atoms Xa and Xb of the compound of formula (I) are identical and chosen from O, S and Se atoms, and preferably Xa=Xb=S.

Advantageously, the aryl or heteroaryl rings $R_1$, $R_2$, $R_3$ and $R_4$ containing 4 to 10 carbon atoms are chosen from phenyl, naphthyl, anthracyl, benzoxazolyl, thiophenyl or alkoxythiophenyl, furyl, pyrrolyl, pyridyl, pyrazyl, pyrazolyl, pyridazyl, pyrimidyl, triazyl, imidazolyl, oxazolyl, indyl, indazolyl, quinolyl and quinoxalyl rings.

Preferably, said rings are identical and chosen from the following phenyl, naphthyl and alkoxythiophenyl rings:

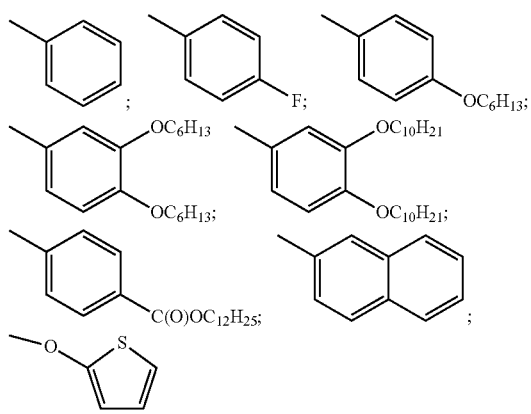

Even more advantageously, the substrate of the invention is coated with a film comprising at least one compound of formula (I) chosen from the following compounds:

Compound (1):

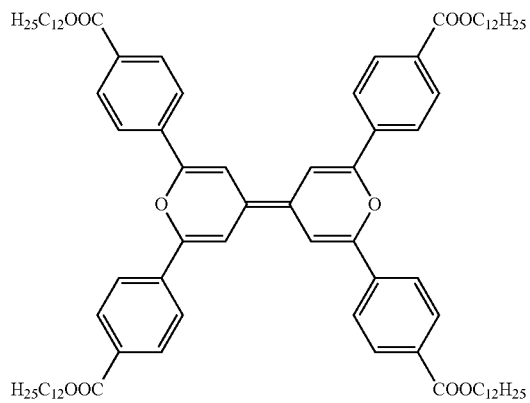

Compound (2):

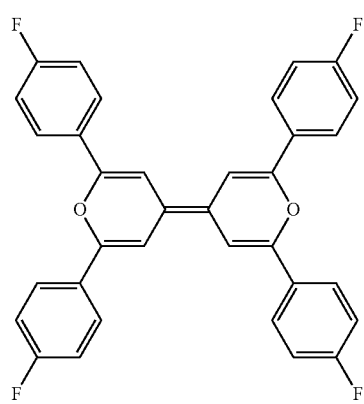

Compound (3):

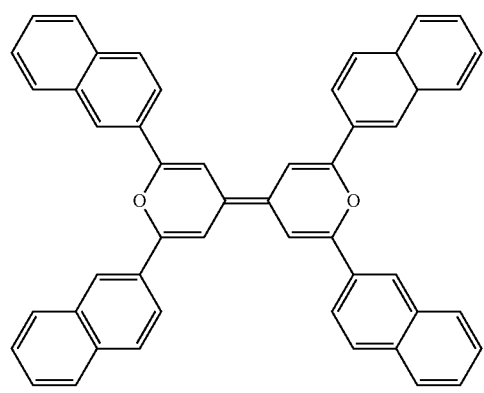

Compound (4):

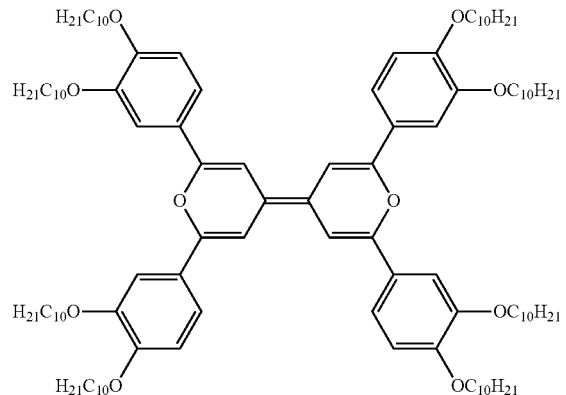

Compound (5):

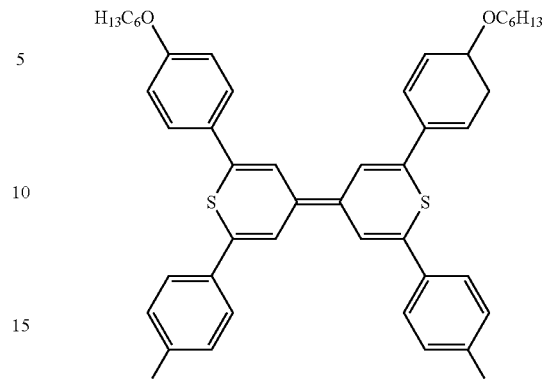

Compound (6):

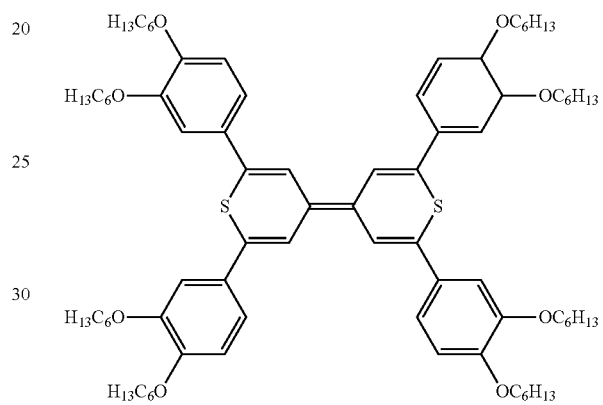

Compound (7):

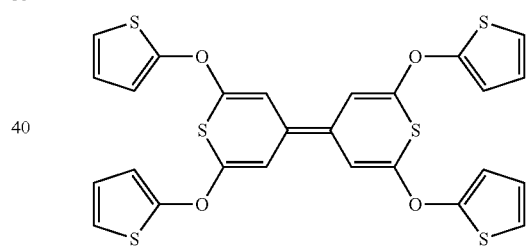

Compound (8):

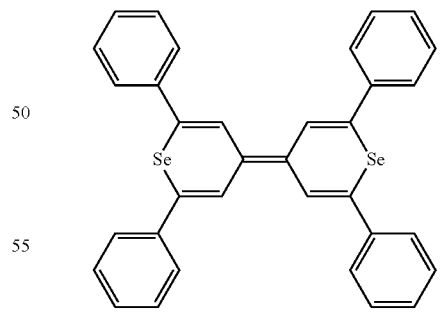

In addition to the compound of formula (I), the film of the invention may also comprise other constituents, and more particularly electron-accepting molecules leading to the formation of charge-transfer complexes, such as 7,7,8,8-tetracyano-p-quinodimethane (TCNQ) or tetrafluoro-7,7,8,8-tetracyano-p-quinodimethane ($F_4$TCNQ). These electron-accepting molecules are introduced in small amount relative to the compound of formula (I). Preferably, the electron-accepting molecules/compounds of formula (I) weight ratio is between 1/99 and 5/95. They act as dopants by increasing the intrinsic hole-conducting properties of the compound of formula (I).

A subject of the present invention is also a process for manufacturing a substrate as defined according to the invention, comprising at least one step of dry-depositing a film comprising a compound of formula (I) as defined above, said deposition being performed at a rate of less than 1 Å/s, preferably less than or equal to 0.4 Å/s and even more preferentially less than or equal to 0.1 Å/s.

The dry deposition is performed by heating under vacuum; it allows the compound of formula (I) to be sublimed. It may be performed via chemical vapor deposition CVD, this technique consisting in adding a metallic precursor to a source of liquid carbon (such as toluene, benzene or cyclohexane), the solution then being transformed into fine droplets, transported by an inert gas to an oven. In practice, the compound of formula (I) is placed, in powder form, in a crucible and then covered with alumina, then heated under vacuum until the compound of formula (I) changes from solid form to liquid form (sublimation). The vapor stream of the compound of formula (I) is then directed toward the substrate so as to cover it with a film formed from the compound of formula (I).

The heating under vacuum, necessary for subliming the compound of formula (I), is preferably performed at a temperature of between 80 and 180° C. and even more preferentially at a temperature of approximately 150° C., at a pressure of between $10^{-4}$ and $10^{-8}$ mbar and even more preferentially at a pressure close to $10^{-6}$ mbar, for a time of between 2 and 4 hours and even more preferentially for a time of approximately 3 hours.

The coated substrate obtained according to this process is constituted of a homogeneous film of high quality, having a high degree of crystallinity. Specifically, the film of the invention is formed from a virtually identical repetition of units (or grains of matter), continuously distributed over the entirety of the substrate, the electrical interface between the substrate and the film being formed from numerous paths for conducting positive charges.

Another subject of the invention relates to the use of a substrate according to the invention as an anode interface layer, and more particularly as a hole-collecting layer, in electronic devices such as organic electroluminescent diodes (OLED), polymeric electroluminescent diodes (PLED), organic field-effect transistors (OFET) and organic solar cells (OSC), the use as an anode in OSCs being particularly preferred.

A further subject of the invention concerns a finished article chosen from OLEDs, PLEDs, OFETs and OSCs, comprising at least one substrate according to the invention. More particularly, a subject of the present invention is also an organic solar cell (OSC), as defined above, in which the substrate is made of oxide, and preferably made of ITO.

Preferably, the organic solar cell (OSC) of the invention comprises at least one base support (a) coated with a substrate (b) as defined according to the invention, said substrate (b) itself being coated with a photosensitive active layer (c).

The base support (a) may be rigid or supple. It is preferably chosen from glass, metals or oxides thereof, and polymers. Preferably, the base support (a) is a metal oxide chosen from aluminum oxide, indium oxide, tin oxide, iridium oxide, silicon oxide, iron oxide and copper oxide, or a polymer chosen from polyethylene terephthalate (PET), amorphous polyethylene (amorphous PE) and amorphous polystyrene (amorphous PS).

The photosensitive active layer (c) is a layer formed from at least two materials that are highly absorbent in the visible region, one being an electron donor and the other an electron acceptor, this layer undergoing ultra-fast charge transfer and creating positive charges (holes) and negative charges (electrons) under the effect of a light irradiation. This photosensitive active layer (c) may be a combination of derivatives of phthalocyanins, of pentacene, of thiophene, of triphenylamine, of polymers of p type, with molecules such as fullerene derivatives or perylenes, the mixture $P_3HT$:PCBM being the preferred combination.

According to one advantageous embodiment, the base support (a) is made of glass, substrate (b) of the invention is made of ITO, and the photosensitive active layer (c) is made of $P_3HT$:PCBM.

The photosensitive active layer (c) may also be coated with a layer (d), also known as the exciton dissociation active layer (or exciton blocking layer EBL), which may be made of lithium fluoride (LiF) in OSC devices or made of alumina in OLED or PLED devices.

The layer (d) may itself also be coated with an electrolytic layer (e) made of on aluminum, gold, calcium, copper, samarium, platinum, palladium, chromium, cobalt or iridium, the layer (e) preferably being made of aluminum.

A subject of the present invention is also a process for manufacturing an organic solar cell (OSC) according to the invention, comprising at least the following steps:

(i) the deposition of a substrate (b) as defined according to the invention onto a base support (a), then (ii) the deposition of a photosensitive active layer (c), said deposition preferably being performed using a spin coater, (iii) optionally, annealing of the photosensitive active layer (c) in a tubular oven, at a temperature of between 30 and 150° C., preferably between 80 and 150° C. and even more preferentially close to 120° C., for a time of between 1 minute and 24 hours, preferably between 5 and 20 minutes and even more preferentially for approximately 10 minutes, under an inert atmosphere of argon, (iv) optionally, the deposition of a layer (d) made of lithium fluoride (LiF), said deposition possibly being performed via a dry route, at an evaporation rate of less than 1 Å/s, preferably less than or equal to 0.4 Å/s and even more preferentially less than 0.1 Å/s, (v) optionally, the deposition of an electrolytic layer (e), said deposition possibly being performed via a dry route, at an evaporation rate of less than or equal to 3 Å/s and preferably between 1 and 2 Å/s.

Advantageously, the layer (d) has a thickness of less than 10 Å, preferably less than 8 Å and even more preferentially between 5 and 7 Å.

Finally, the present invention also protects compounds of formula (I) as such:

Compound (1):

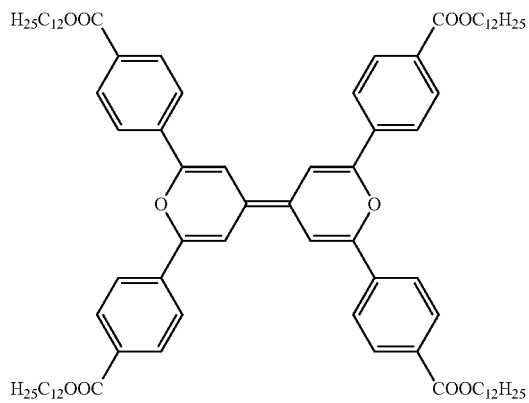

Compound (2):

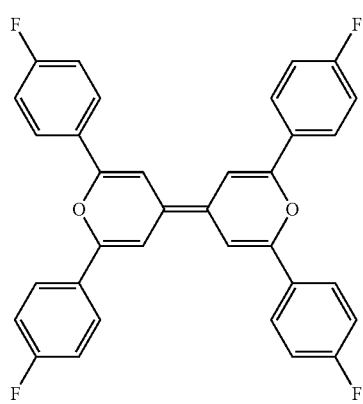

Compound (3):

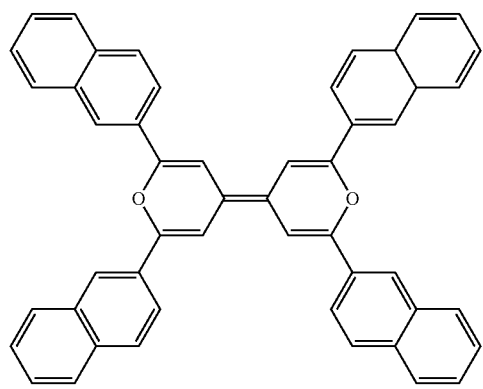

Compound (4):

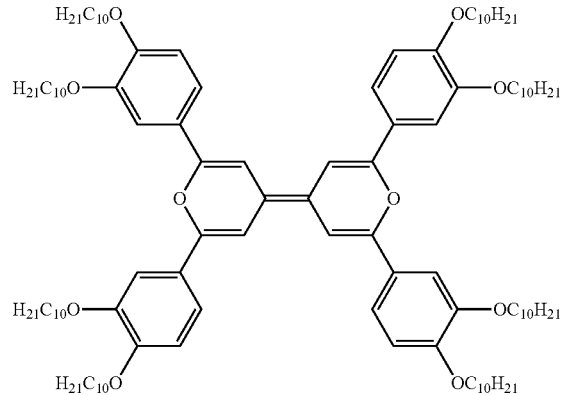

Compound (5):

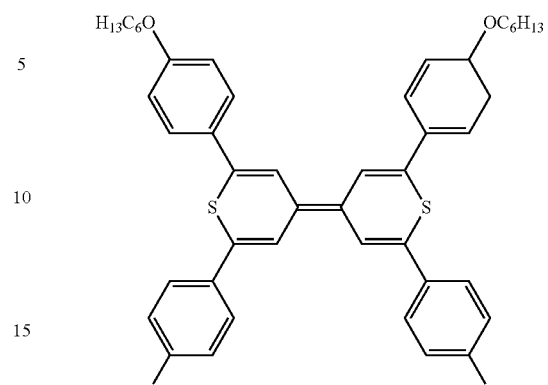

Compound (6):

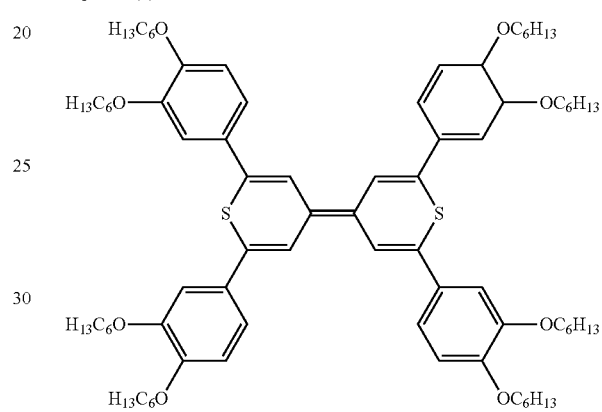

Compound (7):

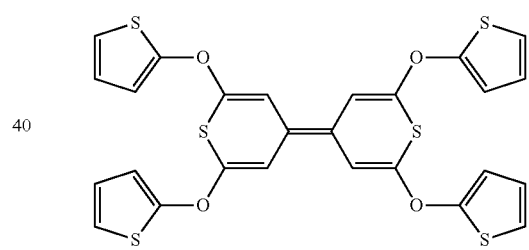

Compound (8):

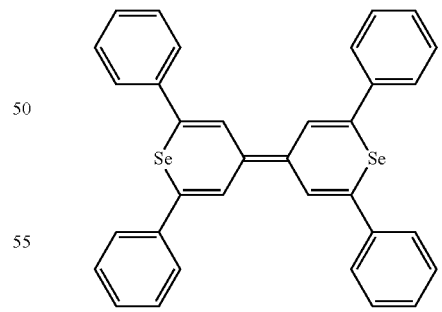

The compounds of formula (I) may be synthesized according to methods known to those skilled in the art, such as those described by Sandman et al., J. Chem. Soc., Chem. Commun., 1977, 687, 177-178, and Otsubo et al., J. Chem. Soc. Perkin Trans., 1993, 1815-1824.

Figure 2:
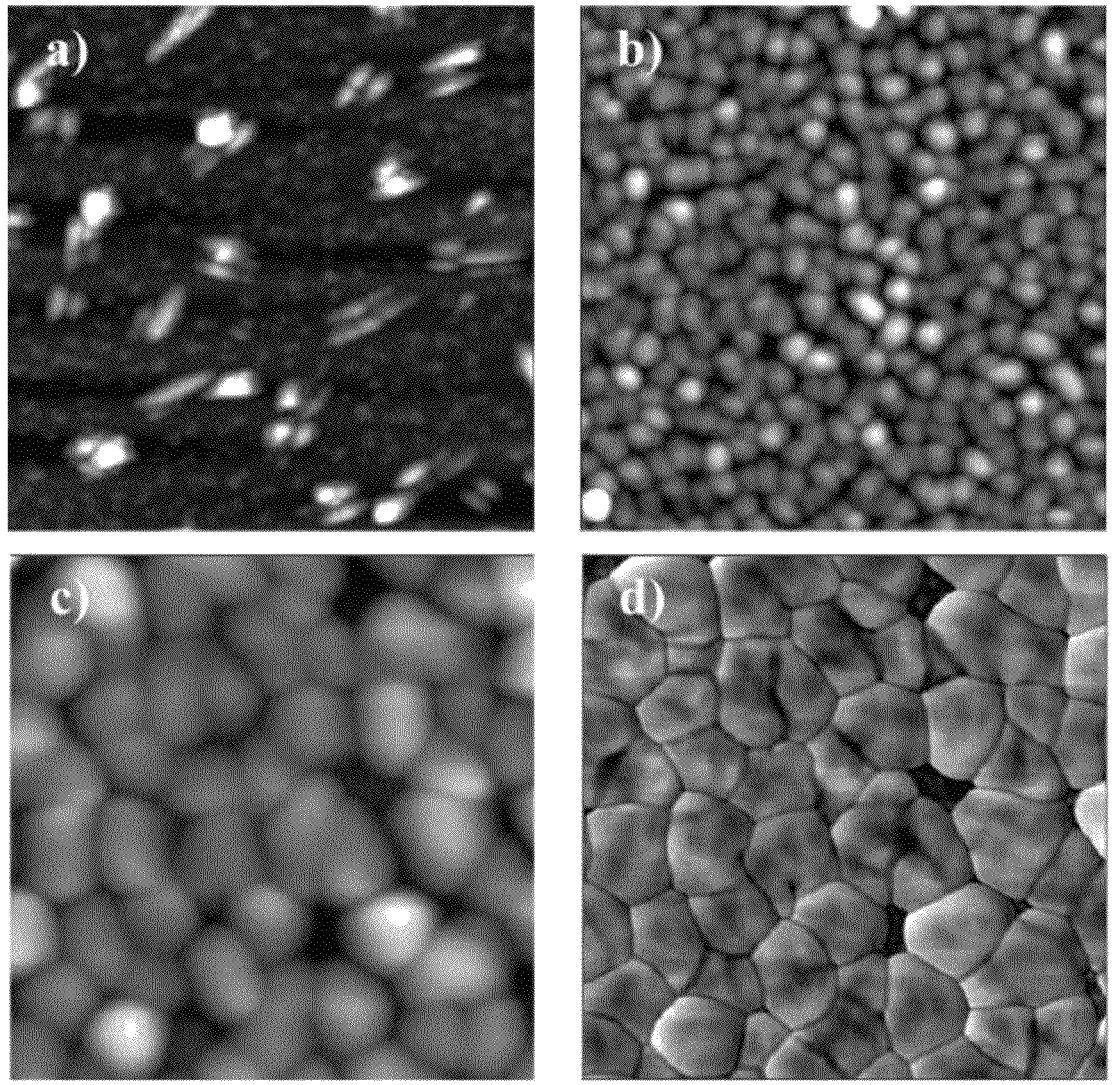
Figure 3:
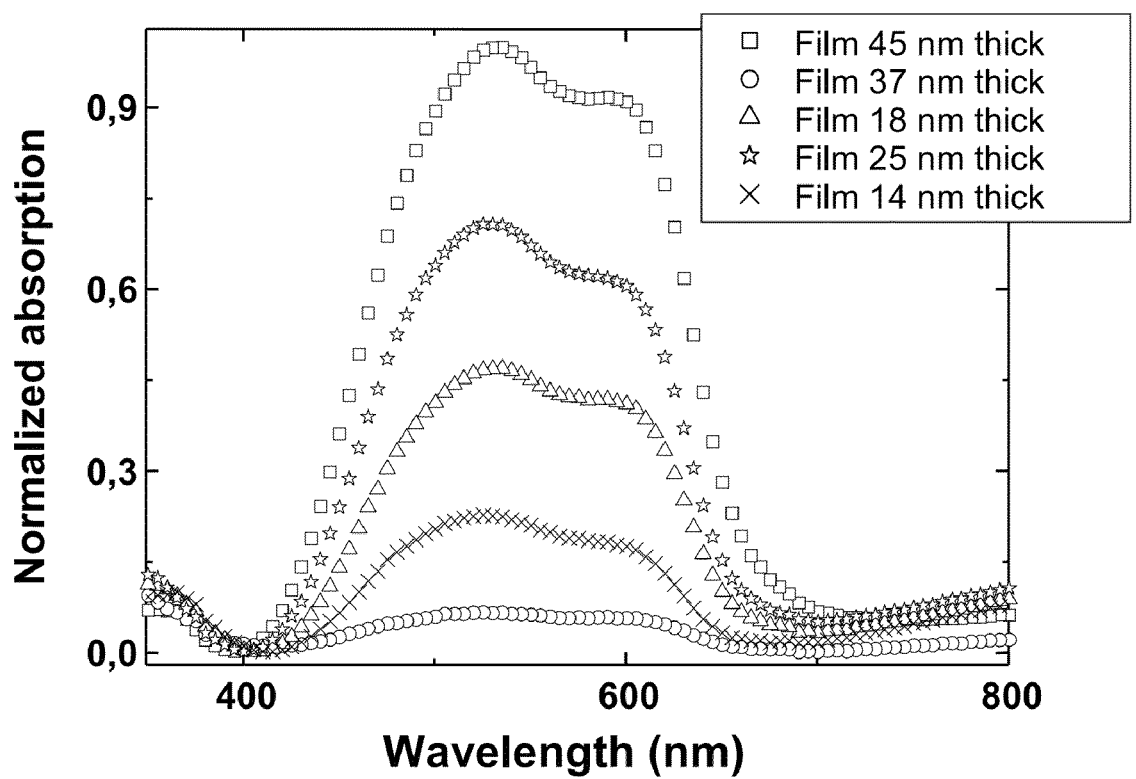
Figure 4:
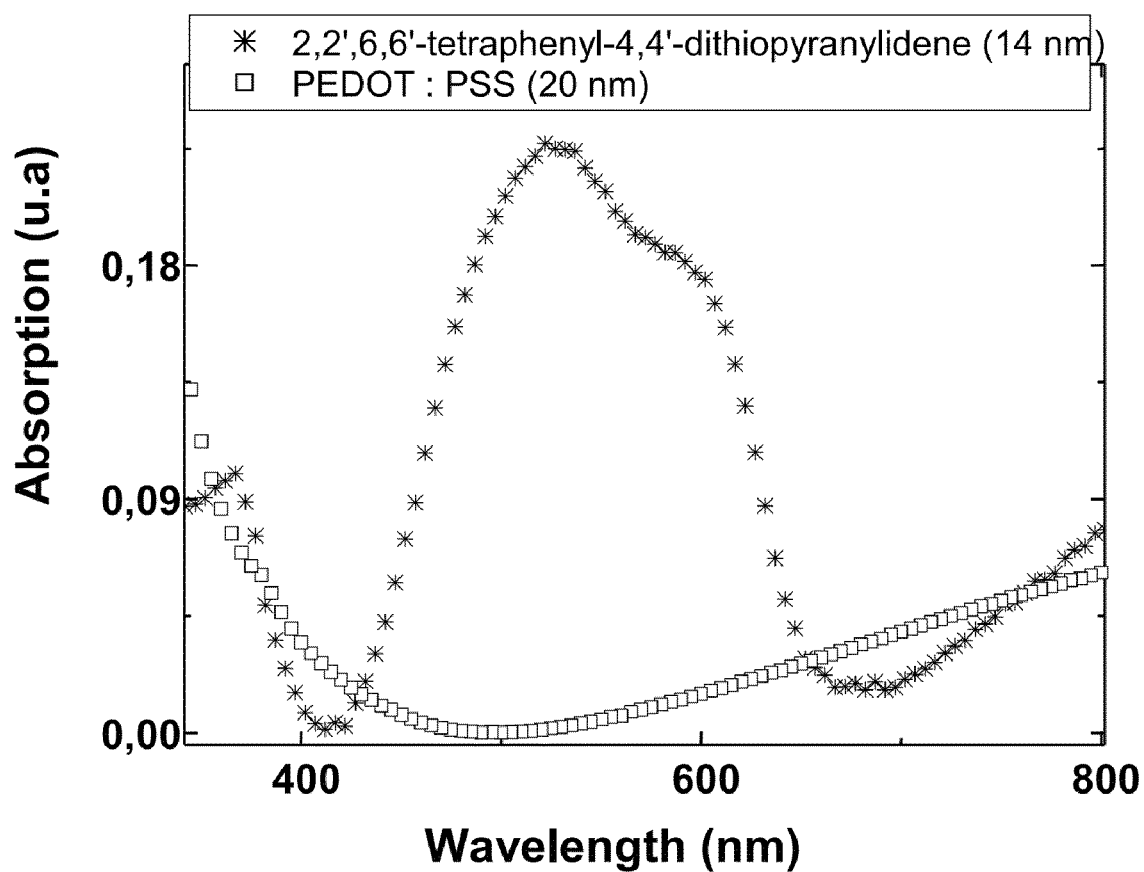
Figure 5:
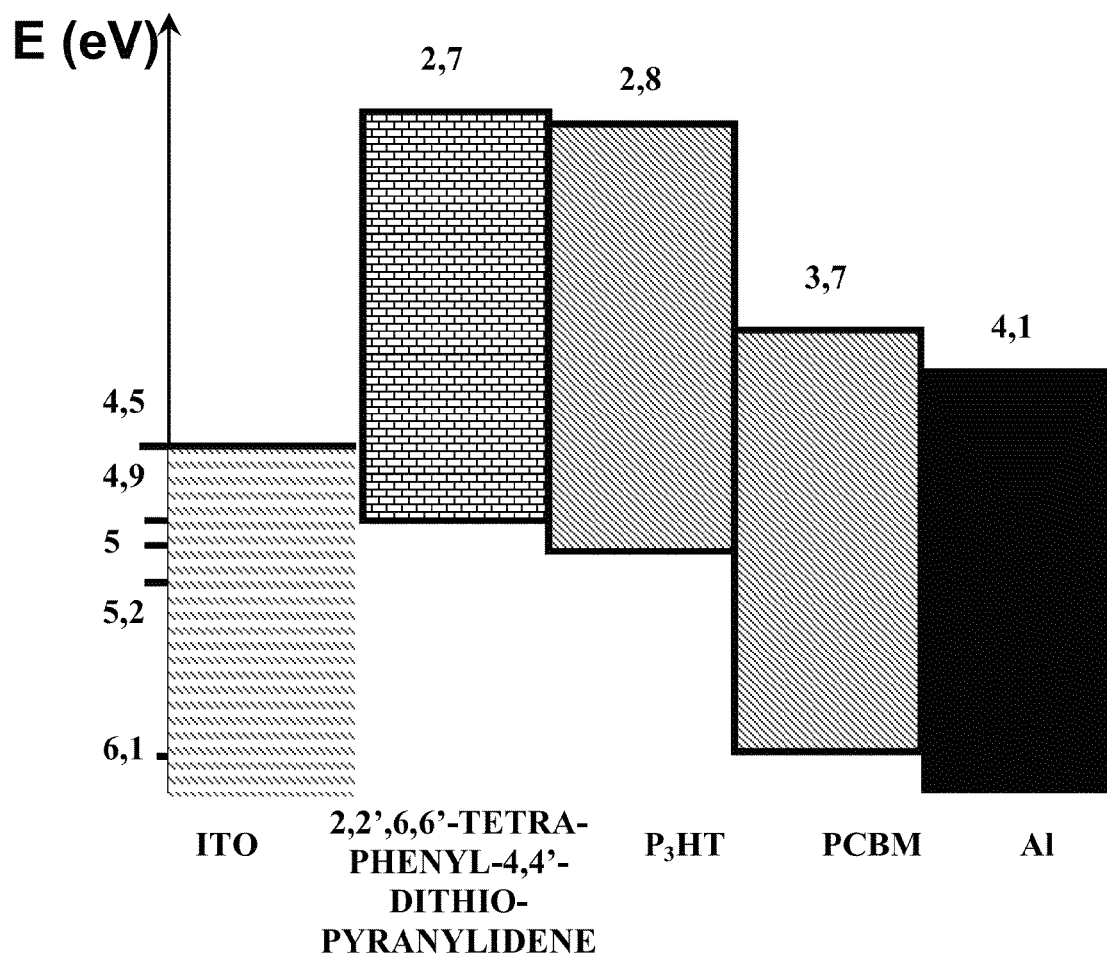
Figure 6:
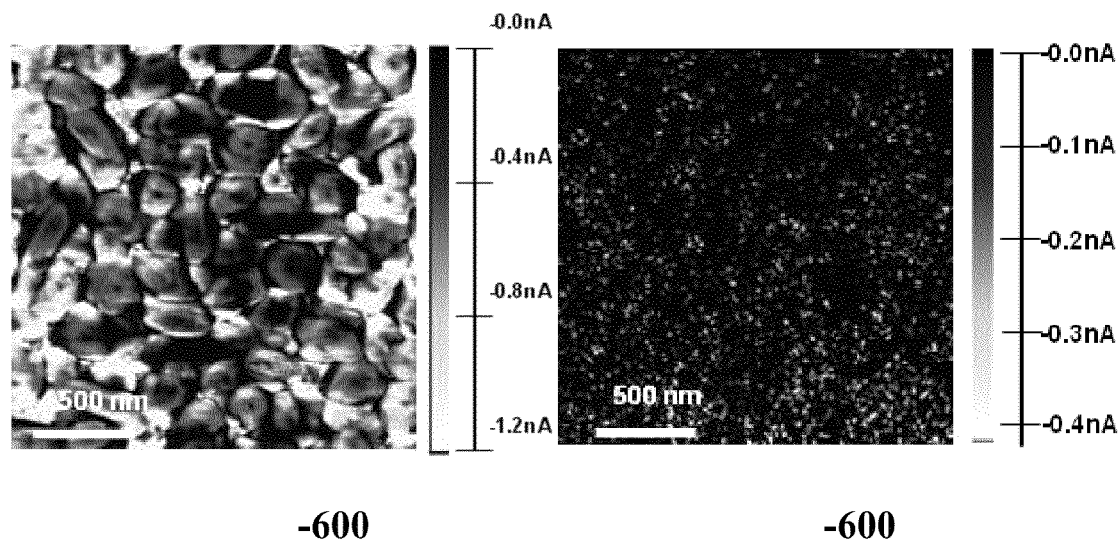
Figure 7:
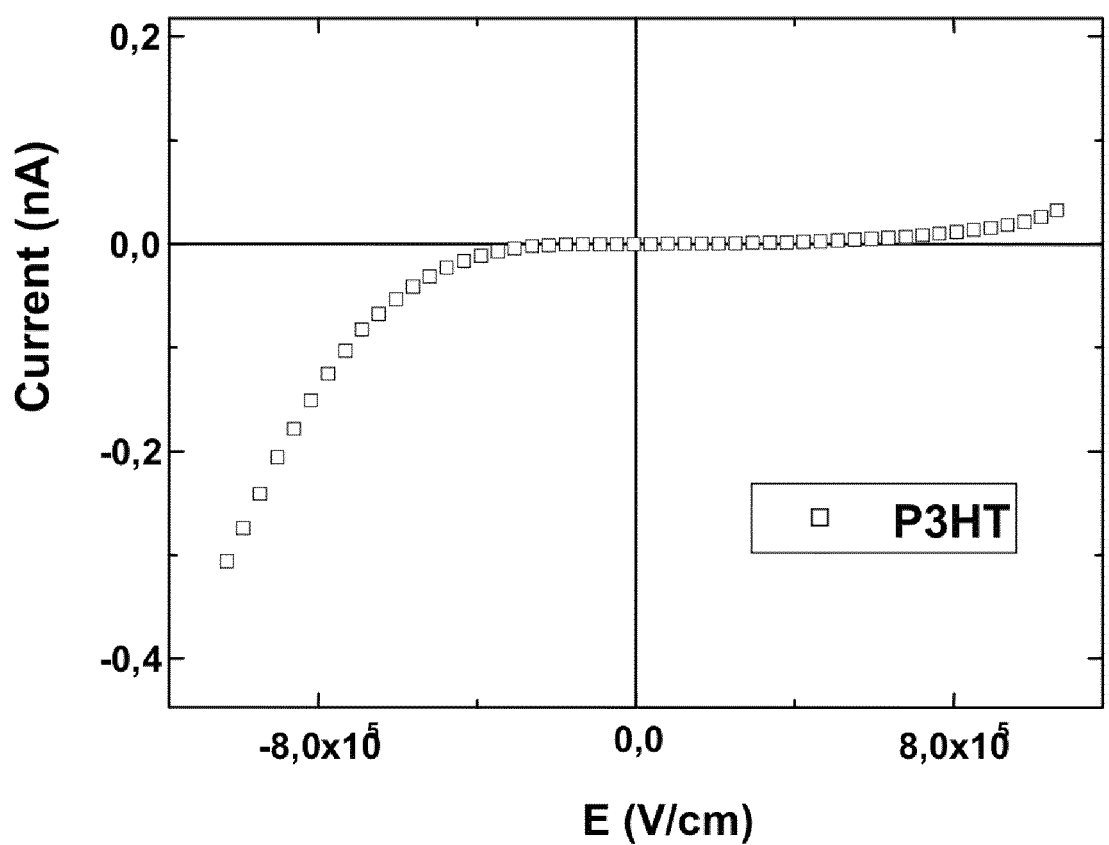
Figure 8:
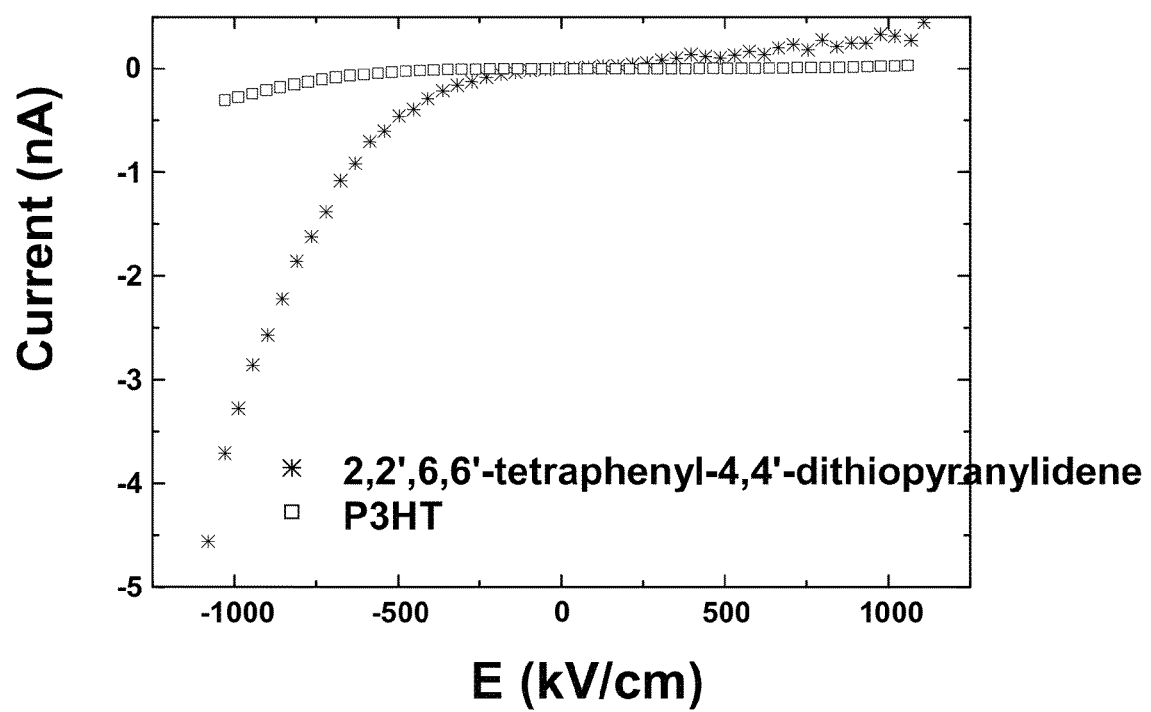
Figure 9:
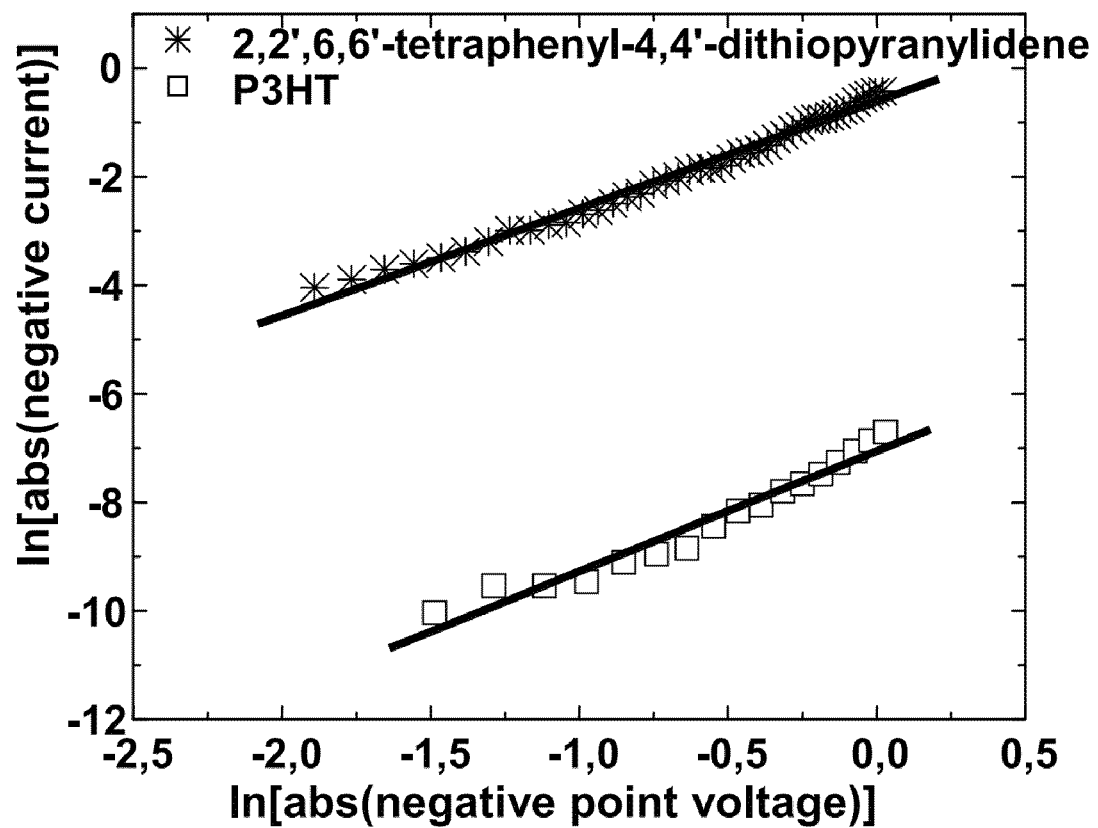
Figure 10:
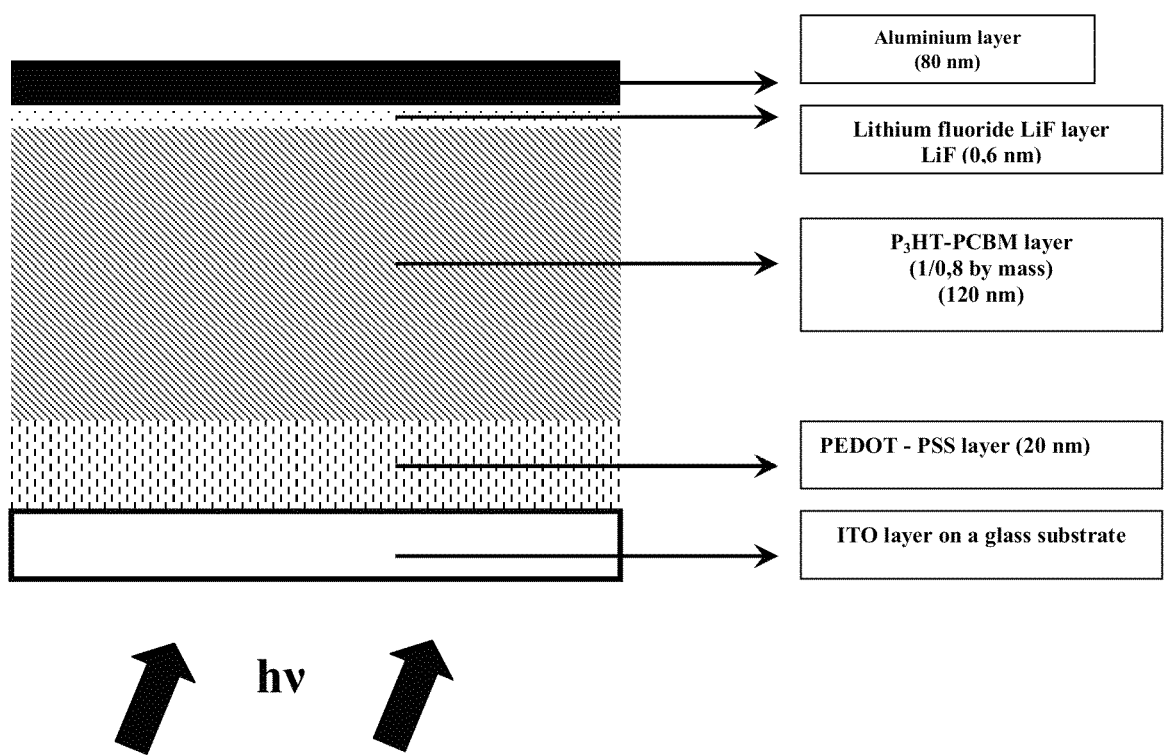
Figure 11:
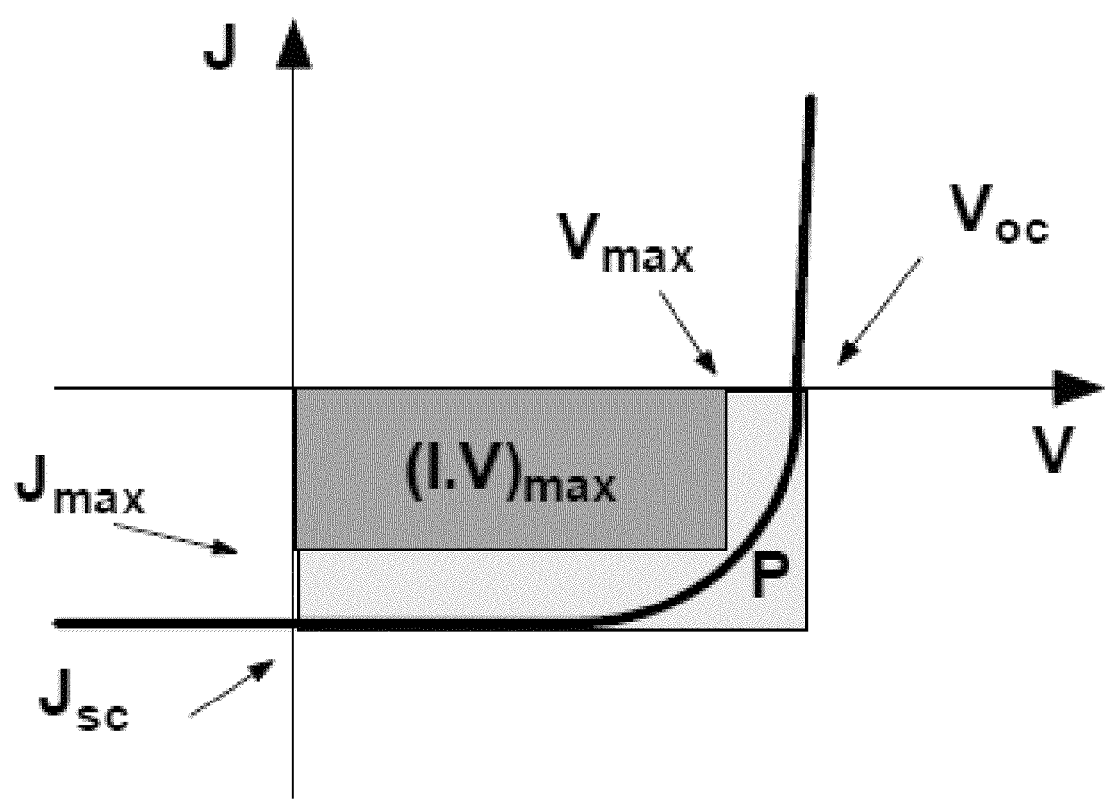
Figure 12:
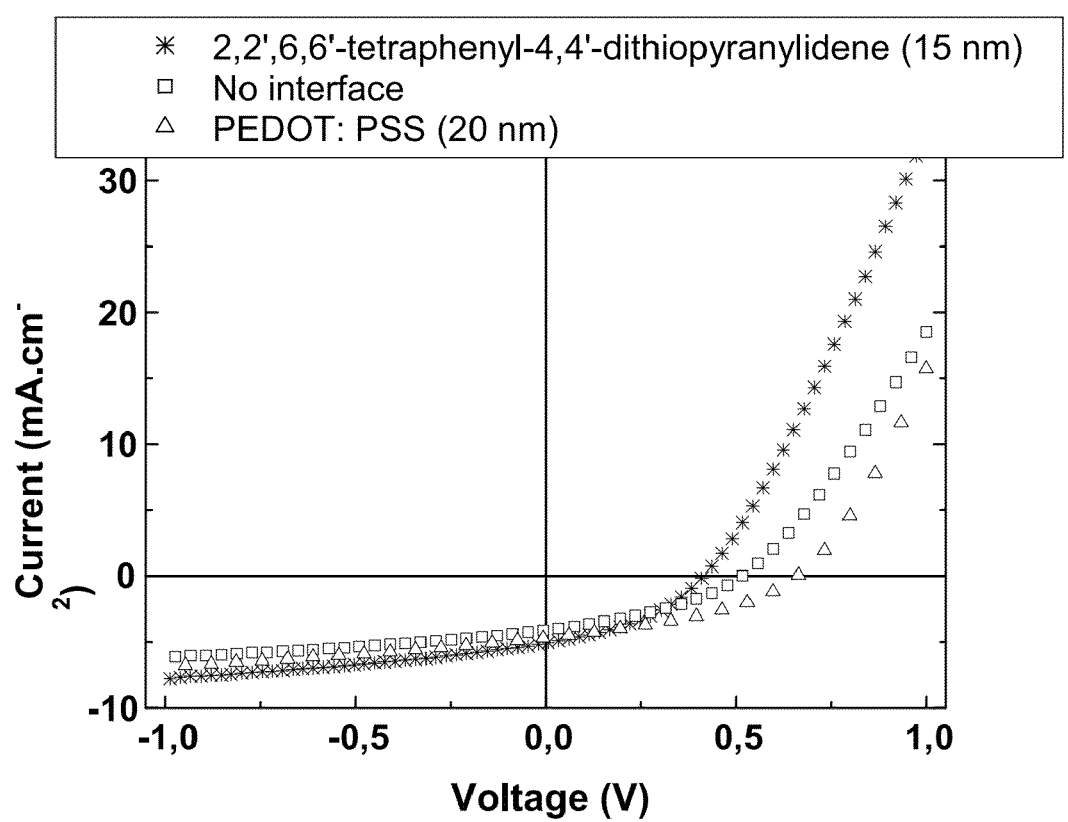
Figure 13:
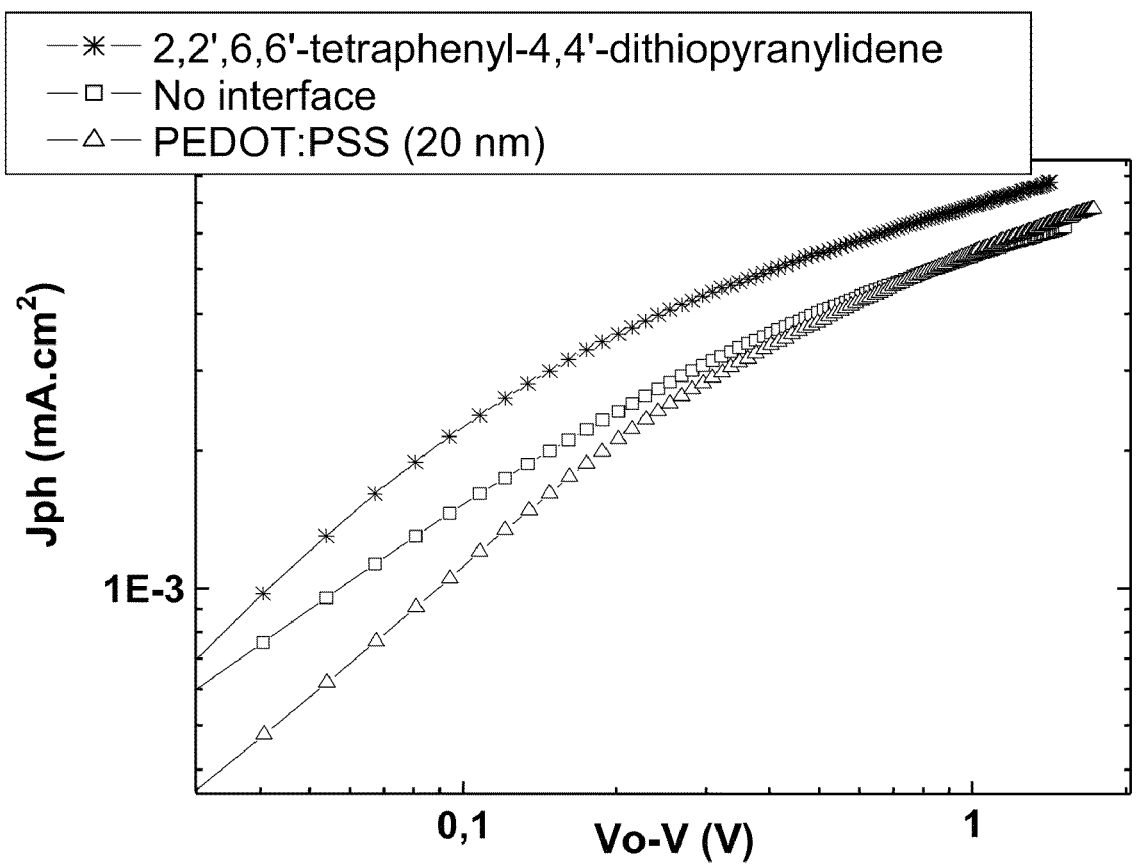
Figure 14:
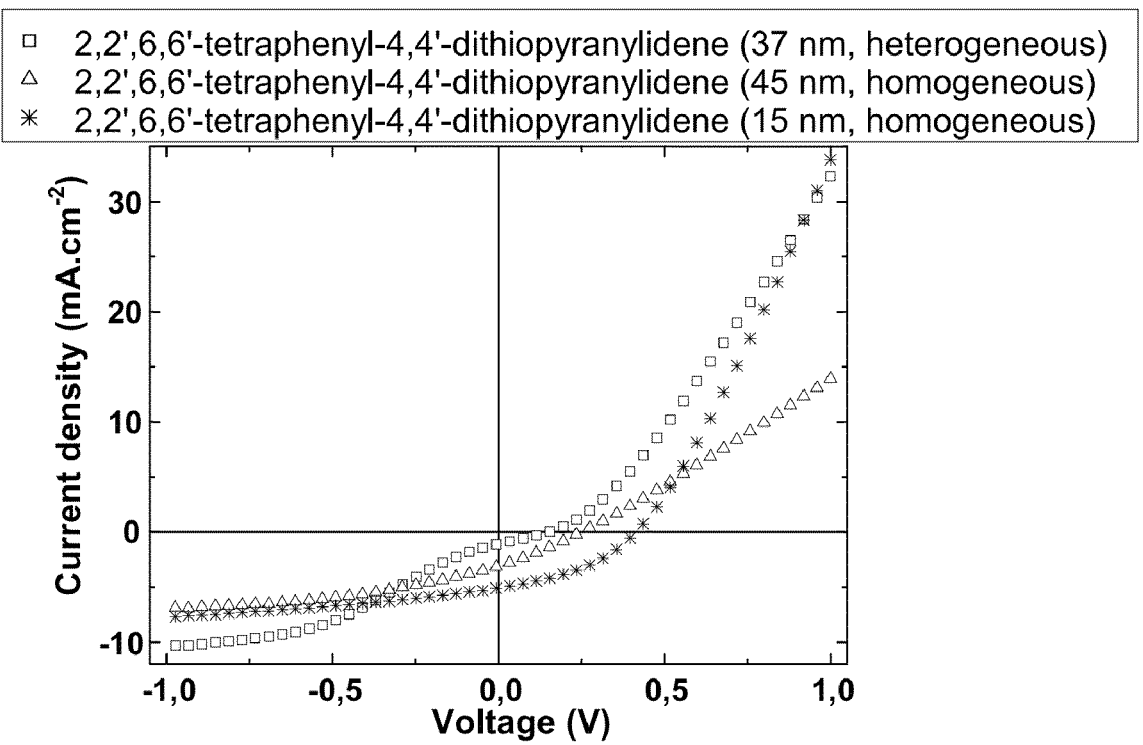
Figure 15:
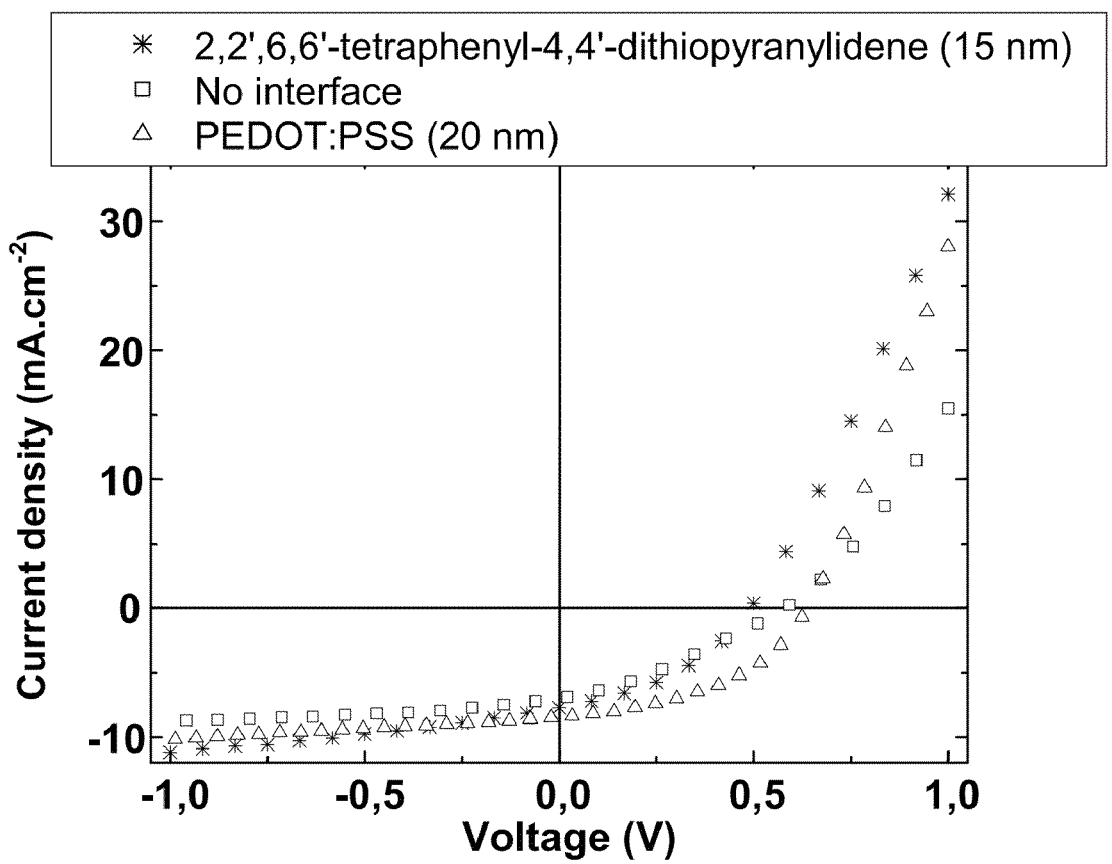
Figure 16:
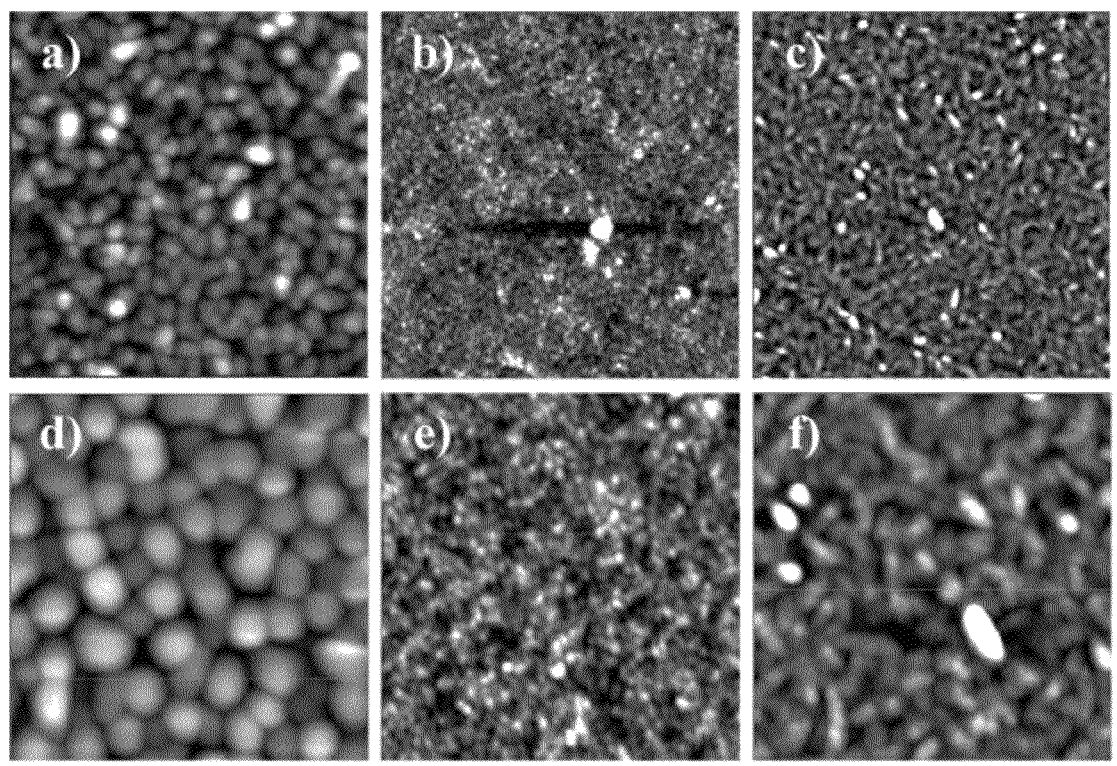

Besides the preceding provisions, the invention also comprises other provisions that will emerge from the description that follows, which refers to examples of implementation and of evaluation of substrates coated with films comprising at least one compound of formula (I) according to the invention, and also to the attached drawings, in which:

FIG. 1 shows images taken with an optical microscope (magnification ×5) of layers prepared via a wet route in different solvents: a) in dichloromethane, b) in toluene, c) in benzene, d) in xylene, e) in chloroform, and f) in tetrahydrofuran, FIG. 2 shows images taken with an atomic force microscope (AFM) in "current sensing" mode of layers prepared according to different evaporation regimes: a) in unstable evaporation regime (5 μm×5 μm), b) in stable evaporation regime (5 μm×5 μm), c) in stable evaporation regime (2 μm×2 μm), and d) phase image, in stable evaporation regime (2 μm×2 μm), FIG. 3 is the absorption spectrum of substrates coated with films made of 2,2',6,6'-tetraphenyl-4,4'-dithiopyranylidene, having different thicknesses, FIG. 4 is the absorption spectrum of a film of 45 nm thick made of 2,2',6,6'-tetraphenyl-4,4'-dithiopyranylidene, and of a film of 20 nm thick made of PEDOT:PSS, FIG. 5 is the energy diagram of the various layers present in a photovoltaic device, FIG. 6 shows images acquired by AFM in "current sensing" mode of a film made of 2,2',6,6'-tetraphenyl-4,4'-dithiopyranylidene and of a film made of PEDOT:PSS, for a potential difference of −600 mV, FIG. 7 shows the change in current as a function of the applied electric field in a P$_3$HT layer, FIG. 8 shows the change in current as a function of the applied voltage for a film according to the invention and for a reference film made of P$_3$HT, these measurements having been determined with a current-sensing atomic force microscope (CS-AFM), FIG. 9 shows the mobility of the positive charges in a film according to the invention and in a reference film made of P$_3$HT, FIG. 10 is a schematic of a reference OSC device comprising an ITO interface covered with a PEDOT-PSS-based conductive polymer and with a P$_3$HT-PCBM-based photosensitive active layer, FIG. 11 states on a graph J=f(V) the manner in which the main characteristics of the photovoltaic devices were determined, FIG. 12 shows the I-V curves for a non-annealed device according to the invention and for two non-annealed reference devices, under lighting, FIG. 13 shows the photocurrent response curves for different diodes, under lighting, FIG. 14 shows the I-V curves for devices comprising substrates coated with films of different thicknesses, under lighting, FIG. 15 shows the I-V curves for an annealed device according to the invention and for two annealed reference devices, under lighting, FIG. 16 shows images acquired by AFM in "current sensing" mode of a film made of 2,2',6,6'-tetraphenyl-4,4'-dithiopyranylidene 14 nm thick [image a) (5 μm×5 μm) and image d) (2 μm×2 μm)], of a film made of PEDOT-PSS 5 nm thick [image b) (5 μm×5 μm) and image e) (2 μm×2 μm)], and of a "hybrid" film comprising a layer made of 2,2',6,6'-tetraphenyl-4,4'-dithiopyranylidene (14 nm thick) coated with a layer of PEDOT-PSS (5 nm thick) [image c) (5 μm×5 μm) and image f) (2 μm×2 μm)].

EXAMPLES

A substrate coated with a film comprising, as compound of formula (I), 2,2',6,6'-tetraphenyl-4,4'-dithiopyranylidene, was prepared according to the procedure described below.

The formula of 2,2',6,6'-tetraphenyl-4,4'-dithiopyranylidene is as follows:

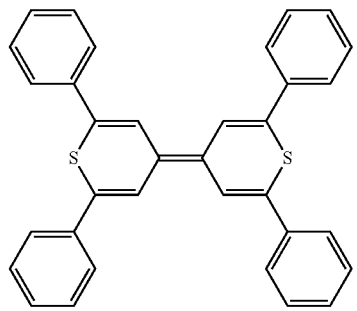 [SMILES: C1=C(c2ccccc2)SC(c2ccccc2)=CC1=C1C=C(c2ccccc2)SC(c2ccccc2)=C1]

A—Synthesis of 2,2',6,6'-tetraphenyl-4,4'-dithiopyranylidene

Compound (I) According to the Invention

Step 1: synthesis of 1,5-diphenyl-1,5-pentanedione

A solution of glutaryl chloride (10 mmol, 1.3 mL) dissolved in anhydrous dichloromethane (20 mL) is introduced into a 100 mL two-necked round-bottomed flask under an inert atmosphere. Aluminum chloride (30 mmol, 4.00 g) is added to the mixture, which immediately turns orange-yellow. A solution of benzene (20 mmol, 1.8 mL) dissolved in anhydrous dichloromethane (10 mL) is added dropwise at room temperature. The solution becomes bright red. The mixture is then refluxed for 24 hours, and turns brown-black. The mixture is then cooled to room temperature and poured into a crystallizing basin containing 20 mL of 10% acidified water, with stirring. A black solid forms, and is filtered off on a Büchner funnel. The yellow organic phase is then extracted with ethyl acetate, dried over MgSO$_4$, filtered, concentrated on a rotary evaporator and recrystallized from 20 mL of methanol. The product obtained is a white solid in a mass of 680 mg. The reaction yield is 27%.

TLC (eluent: 1/1 petroleum ether/ethyl acetate): 0.75

$^1$H NMR (CDCl$_3$, 400 MHz): δ=7.98 (d, 4H, $^3$J=7.1 Hz), 7.57 (t, 2H, $^3$J=7.3 Hz), 7.47 (t, 4H, $^3$J=7.3 Hz), 3.13 (t, 4H, $^3$J=6.9 Hz), 2.21 (quint., 2H, $^3$J=6.9 Hz)

Step 2: synthesis of 2,6-diphenylthiopyrylium perchlorate

The 1,5-diphenyl-1,5-pentanedione prepared in step 1 (10 mmol, 2.52 g) is mixed with phosphorus pentasulfide (15 mmol, 3.34 g), acetic acid (60 mL) and lithium perchlorate (60 mmol, 6.40 g) in a 100 mL two-necked round-bottomed flask, and then refluxed for 3 hours. The solution then becomes orange and a white precipitate forms. The precipitate is removed by filtration on a sinter funnel and then washed with hot acetic acid. The solution is concentrated on a rotary evaporator and recrystallized by addition of ether (500 mL). The precipitate obtained is filtered off on a sinter funnel and then dried on a rotary evaporator. The product obtained is a yellow solid in a mass of 850 mg. The reaction yield is 24%.

TLC (eluent: 8/2 petroleum ether/ethyl acetate): 0.0

$^1$H NMR (D$_2$O, 400 MHz): δ=8.80 (m, 3H), 7.92 (d, 4H, $^3$J=7.3 Hz), 7.68 (t, 2H, $^3$J=7.3 Hz), 7.60 (t, 4H, $^3$J=8.0 Hz)

Step 3: synthesis of 2,2',6,6'-tetraphenyl-4,4'-dithiopyranylidene

The 2,6-diphenylthiopyrylium perchlorate (10 mmol, 3.50 g) is dissolved in 200 mL of distilled acetone in a 250 mL two-necked round-bottomed flask, and the mixture is then refluxed for 2 hours under an inert atmosphere. Zinc powder (30 mmol, 1.96 g) is added portionwise and the mixture is refluxed for a further 24 hours. The solution is filtered, rinsed with toluene and evaporated on a rotary evaporator. A black oil is obtained, which is recrystallized from a 1/1 hexane/ethanol mixture. A black solid is obtained in a mass of 650 mg. The reaction yield is 13%.

TLC (eluent: 8/2 petroleum ether/ethyl acetate): 0.64

IR (cm$^{-1}$): 3018, 1735, 1570, 1488, 1441, 1229, 1071, 750, 682

B—Manufacture and Use of the Substrates of the Invention

The 2,2',6,6'-tetraphenyl-4,4'-dithiopyranylidene was applied to an ITO electrode, which was itself applied to a glass-based support, according to two different techniques:
- a wet-route deposition, and
- a dry-route deposition.

Images of these substrates, acquired using an optical microscope and by AFM, are shown in FIGS. 1 and 2.

The wet-route deposition was performed by spin coating in various solvents, by depositing a concentrated solution of compound of formula (I) onto a substrate rotating at 2000 rpm for 50 seconds. Due to the low solubility of 2,2',6,6'-tetraphenyl-4,4'-dithiopyranylidene in the usual solvents, the films formed and evaluated were nonuniform (presence of needles 50 nm to 300 μm long and 1 to 15 μm in diameter—cf. FIG. 1), irrespective of the conditions used (concentration, nature of the solvent, preparation method).

The dry-route deposition was performed by MO-CVD (Metal Organic Chemical Vapor Deposition). The films obtained were observed by AFM and are shown in FIG. 2. The morphology of the films obtained is highly influenced by the evaporation regime. The most uniform deposits are obtained for stable evaporation rates (0.1 Å/s). The films have "monodisperse" distributions of 2,2',6,6'-tetraphenyl-4,4'-dithiopyranylidene particles with a mean diameter of about 200 nm. The evaporation regime is considered as unstable when the evaporation rate during the application is, at any given moment, greater than 1 Å/s.

Table I hereinbelow illustrates the characteristics of several substrates coated with films comprising 2,2',6,6'-tetraphenyl-4,4'-dithiopyranylidene, showing the influence of the thickness and of the evaporation regime (dry-route deposition) on the RMS (root mean square) roughness of the films.

TABLE I

| Evaporation regimes | Film thicknesses | RMS roughnesses |
|---|---|---|
| Stable (evaporation rate = 0.1 Å/s) | 14 | 5.5 |
| | 18 | 5.1 |
| | 25 | 9.05 |
| | 45.1 | 12.5 |
| Unstable (evaporation rate = 1.5 Å/s) | 37 | 18.7 |

The RMS roughness corresponds to the measurement of the heights of all of the grains present in the film (accessible by AFM), relative to the mean of these values: this is a mean standard deviation of the heights. The more this value tends toward 0, the closer the heights of the grains become, and the more the film is considered as uniform.

In conclusion, a dry-route deposition under a stable evaporation regime makes it possible to obtain thermally polycrystalline monodisperse layers.

C—Evaluation of the Optical Properties of the Substrates of the Invention

Absorption spectra obtained for different film thicknesses are shown in FIG. 3.

The absorption spectra obtained show two maxima located, respectively, at 530 nm and 595 nm. The first maximum corresponds to a π→π* transition, whereas the second maximum appears to demonstrate an internal charge transfer in the 2,2',6,6'-tetraphenyl-4,4'-dithiopyranylidene organic layer, thus demonstrating the high degree of crystallinity of the film formed.

It is observed that the absorption of the layers increases as their thickness increases (the thickness measurements determined by AFM are thus qualitatively confirmed). An exception to this law is observed for the film having a thickness of 37 nm obtained from an evaporation under an unstable regime.

The absorption spectrum of a film according to the invention was also compared with the absorption spectrum of a representative PEDOT-PSS film of the prior art (cf. FIG. 4). The absorption of the film according to the invention is high and much more intense than that of the PEDOT-PSS film, especially for wavelengths located in the visible region.

D—Evaluation of the Electronic Properties of the Substrates of the Invention The energy levels of the 2,2',6,6'-tetraphenyl-4,4'-dithiopyranylidene molecule were determined by cyclic voltammetry. These measurements were taken at a sweep speed of 0.1 V/s. The working electrode used is a platinum electrode. The potential measurements were taken relative to a reference saturated calomel electrode.

2,2',6,6'-tetraphenyl-4,4'-dithiopyranylidene shows two reversible oxidation waves located, respectively, at 330 mV and at 550 mV. The fact that the oxidation waves are reversible suggests that the oxidized molecule is stable throughout the measurement.

The values for the oxidation waves obtained are relatively low and the difference between the two oxidation peaks is 220 mV, which allows determination of the HOMO level of the molecule (energy level of the highest occupied molecular orbital) according to two different methods (D'Andrade et al., Organic Electronics 6, 2005, 11-20):

Formula 1: $E_{HOMO} = -(1.4 \pm 0.1) * q * Vcv - (4.6 \pm 0.08)$
$E_{HOMO} = (-4.806/-5.01)$ eV
in which:
q corresponds to the electronic charge and is equal to 1, and
Vcv corresponds to the difference between two oxidation potentials and is equal to 0.22 eV Formula 2: $E_{HOMO} = -4.72 -$ (value of the first oxidation potential)
$E_{HOMO} = -5.05$ eV.

Table II below collates all of the energy values obtained for 2,2',6,6'-tetraphenyl-4,4'-dithiopyranylidene (according to different techniques, the UPS technique being Ultraviolet Photoemission Spectroscopy).

TABLE II

| Anode interface layer | Measuring technique | HOMO (eV) | LUMO (eV) | Difference (eV) |
|---|---|---|---|---|
| Isolated 2,2',6,6'-tetra-phenyl-4,4'-dithio-pyranylidene (dissolved in tetrahydrofuran) | Molecular modeling | −4.38 | −1.90 | 2.48 |
| | UV-Visible absorption on solution | — | — | 2.62 |
| | Cyclic voltammetry (Formula 1) | −4.8/−5.0 | — | — |
| | Cyclic voltammetry (Formula 2) | −5.05 | — | — |
| 2,2',6,6'-tetraphenyl-4,4'-dithiopyranylidene-based film | UV-Visible absorption on film | — | — | 2.08 |
| | UPS | −4.8/−4.9 | — | — |
| ITO | UPS | −4.45/−4.55 | — | — |
| PEDOT-PSS | UPS | −5.2 | — | — |

The various values obtained make it possible to draw the energy diagram of FIG. 5.

It is thus seen that 2,2',6,6'-tetraphenyl-4,4'-dithiopyranylidene has energy levels intermediate between the Fermi level of ITO and that of poly(3-hexylthiophene) ($P_3HT$) and methyl[6,6]phenyl-$C_{61}$-butyrate (PCBM), $P_3HT$/PCBM constituting the photosensitive active layer. The energy barrier allowing the passage of positive charges is lowered at the anode, which makes it an excellent candidate for the collection of holes in photovoltaic devices.

Since the energy conditions are favorable to the use of derivatives of dipyranylidene type at the anode interface, the capacity of 2,2',6,6'-tetraphenyl-4,4'-dithiopyranylidene to conduct charges (hole mobility) was also evaluated in order to assert the possible efficacy of this interface.

Study of the Injection of Charges into 2,2',6,6'-tetraphenyl-4,4'-dithiopyranylidene Films by Current-Sensing AFM:

Comprehension of the effects of structuring of the surfaces used in photovoltaic devices was studied by current-sensing atomic force microscopy (CS-AFM), this method making it possible concomitantly to measure the vertical charge transport properties via local measurements of current-voltage (I-V) and to take topography images of the studied layers.

a) Principle of the CS-AFM Local Probe Measurements

All the measurements were taken using a PicoLE microscope (Molecular Imaging), equipped with a current-sensing nozzle (preamplifier gain=1 nA/V and current range ±10 nA). For these measurements, the microscope is used in "Contact" mode.

The points used have a $PtIr_5$ conductive coating with a stiffness constant of 0.2 N/m and a radius of 25 nm, and are connected to a virtual ground via the preamplifier.

For the measurements, the conductive point used is in contact with the surface of the substrate (the point in fact acts as a nanoelectrode) and measures the current response as a function of the applied voltage at different points on the substrate (I-V curves). The voltage is applied to the ITO conductive substrate and the current is measured via the preamplifier. For each of the substrates, more than 200 I-V curves are collected at different locations in order to establish an average of the results.

The morphology of the 2,2',6,6'-tetraphenyl-4,4'-dithiopyranylidene layers could thus be correlated to the charge transport regime, and the charge mobilities of the film were able to be determined by comparison with a known reference, i.e. $P_3HT$.

Two types of layer were studied:
a $P_3HT$ layer 47 nm thick, which serves as reference for calculating the mobilities, this layer having been obtained from a $P_3HT$ solution at 15 mg/mL in chlorobenzene. To do this, 15 mg of $P_3HT$ powder are dissolved in 1 mL of chlorobenzene, the solvent is then filtered through a Teflon® filter with pores 200 μm in diameter, and the $P_3HT$ solution is placed in a sonication bath for 2 hours at room temperature. 10 μL of this solution are then deposited by spin coating onto an ITO substrate of dimensions 1 cm×2.5 cm (at a rate of 2000 rpm for 50 seconds). No annealing was performed on this substrate and no PEDOT-PSS layer was deposited between the ITO substrate and the layer of $P_3HT$. The thickness of 47 nm was successively determined with a Dektak profilometer, and then by current-sensing AFM, 2,2',6,6'-tetraphenyl-4,4'-dithiopyranylidene layers of different thicknesses, the compound of the invention having been applied to ITO substrates by MO-CVD, at a stable evaporation regime of 0.1 Å/s. The thicknesses were also determined with a Dektak profilometer and by current-sensing AFM.

b) Two-Dimensional Mapping of the Electrical Properties of the Substrates of the Invention The 2,2',6,6'-tetraphenyl-4,4'-dithiopyranylidene-based films, obtained under a stable evaporation regime of 0.1 Å/s, have similar morphologies and are composed of particles with a diameter of about 200 nm (cf. above).

FIG. 6 shows a 2,2',6,6'-tetraphenyl-4,4'-dithiopyranylidene film and a PEDOT-PSS-based film, taken by AFM in current-sensing mode, for a potential difference of −600 mV. The image associated with the 2,2',6,6'-tetraphenyl-4,4'-dithiopyranylidene layer reveals many current contrasts, corresponding to the preferential hole conduction paths. These current contrasts appear starting at low polarization values, which means that the resistances associated with the bulk of the organic layer are low. For the same potential difference of −600 mV, it is observed that the conduction paths are far fewer and less intense in the case of PEDOT-PSS. The hole collection is thus more pronounced in the case of the film of the invention.

c) Characterization of the Charge Injection Regime In the Case of $P_3HT$ (Reference):

Local current measurements were taken on a layer of $P_3HT$ and are shown on the graph of FIG. 7.

The curve obtained is divided into two asymmetric regions: a hyperbolic variation of the current for negative voltages of the ITO substrate and a very low current for positive voltages are distinguished thereon. This asymmetric and hyperbolic dependence of the current indicates charge transport dominated by a charge space area defined according to the Mott-Gurney law:

$$J = 9/8 \in_r \in_o \mu (V^2/L^3)$$

in which:
- J is the measured charge density, where J=I/S (I is the current directly measured by the preamplifier and S=100 nm² is the area of contact between the point and the substrate, calculated from the Hertz model),
- $\in_r$ is the dielectric constant of the polymer, taken to be equal to 3,
- $\in_o$ is the relative permittivity of a vacuum, taken to be equal to $8.854187\times10^{-12}$ m$^{-3}$·kg$^{-1}$·s$^4$·A$^2$,
- µ represents the charge mobility,
- V is the applied potential (between 2 V and −2 V), and
- L is the thickness of the P₃HT film (e=47 nm).

This law makes it possible to calculate the maximum charge flow that can pass through a plane geometry.

In the Case of 2,2',6,6'-Tetraphenyl-4,4'-Dithiopyranylidene:

Local current measurements were taken by CS-AFM on substrates according to the invention coated with 2,2',6,6'-tetraphenyl-4,4'-dithiopyranylidene-based films, and are compared with those obtained for the reference P₃HT (cf. FIG. 8). The curve obtained for the film of the invention is divided into two regions in which the current passes differently. This behavior suggests that the film of the invention is a semiconductive film of p type and confirms that its HOMO energy level is between the output work values of Pt and of the ITO substrate.

The calculated positive charge mobilities are shown in FIG. 9 and are greater by a factor of 10 than those obtained for P₃HT.

E—Application to OSC Devices

An OSC device comprising an ITO substrate coated with a film according to the invention (device 1) was compared with:
- a reference OSC device comprising only an ITO substrate and a photosensitive active layer (device 2), and
- a reference OSC device comprising an ITO substrate coated with a PEDOT-PSS-based conductive polymer, and then with a photosensitive active layer (device 3).

These three devices are represented schematically in FIG. 10.

Manufacture of the OSC Device of the Invention (Device 1):

ITO substrates (Sigma-Aldrich) having a resistivity of about 40 Ω·cm$^{-2}$ are etched and washed according to the protocol described below.

2.2 cm×2.5 cm substrates are cut out with a diamond-tipped pen, the residual glass particles are removed with a stream of air localized on the cuts, and the substrates obtained are washed with soapy water and dried at room temperature. A conductive track is then inscribed in the centre of the substrates by ITO etching: after partially covering with a strip of adhesive tape, the substrates are immersed in a solution comprising 20 mL of concentrated (47%) hydrochloric acid, 20 mL of distilled water and about 2 g of iron chloride. This electrochemical process allows removal of the ITO not covered by the adhesive tape, the etched substrates then being washed three times successively with soapy water and with distilled water. The adhesive tape residues are then removed. After drying with a stream of air, the substrates are immersed in two sonication baths at room temperature for 10 minutes: the first bath being an acetone bath, and the second an ethanol bath. The substrates are then dried with a stream of nitrogen and then placed under a UV lamp to undergo etching for 20 minutes with ozone: the lamp degrades the oxygen molecules that enter the chamber, the ozone formed being a powerful oxidizing agent that removes the final carbon-based contamination originating from the ambient air. The treated substrates are then removed from the chamber and used immediately.

The compound of formula (I) is then placed on the freshly treated ITO substrates, said deposit being performed via a dry route at a temperature of about 150° C. under a pressure of 10$^{-6}$ mbar, for a period of 3 hours.

A photosensitive active layer formed from a volume mixture of P₃HT-PCBM (Sigma-Aldrich) (weight ratio: 1/0.8) in 1 mL of chlorobenzene is deposited by spin coating, at a rate of 1000 rpm for 20 seconds, and then at 1400 rpm for 20 seconds, and finally at 1000 rpm for 10 seconds, so as to obtain a layer 110 nm thick. Annealing at 120° C. in a tubular oven under an argon atmosphere may optionally be performed (see hereinbelow). The annealing makes it possible to optimize the morphology and the internal structure of the active layer, thus increasing the photovoltaic performance of the OSC device.

Lithium fluoride LiF (Sigma-Aldrich) is then thermally evaporated under a stable evaporation regime of 0.1 Å/s until a layer with a thickness of between 5 and 7 Å is obtained.

Aluminum electrodes 80 nm thick are then thermally deposited under a stable evaporation regime of between 1 and 2 Å/s and at a pressure of 10$^{-6}$ mbar.

Manufacture of the Reference OSC Devices (Devices 2 and 3):

Devices 2 and 3 were prepared according to the same protocol as described previously (cf. device 1).

For device 2, the photosensitive active layer was deposited directly onto an ITO substrate.

For device 3, a PEDOT-PSS conductive polymer (Sigma-Aldrich) is deposited by spin coating at a rate of 2000 rpm for 50 seconds, and then annealed for 30 minutes at 120° C. in a tubular oven under an argon atmosphere, so as to obtain a film 20 nm thick.

Compared Photovoltaic Properties of Devices 1, 2 and 3, without Annealing of the Active Layer:

a) Characteristics in the Dark

The characteristics in the dark are determined by placing a black cloth on the devices.

In the dark, a solar cell follows the behavior of a standard diode. Depending on whether the applied voltage is greater or less than a threshold voltage, the diode is, respectively, "passing" or "blocking". The current $I_d$ in the diode follows an equation of Shockley type:

$$I_d=I_s(\exp(eV/nkT)-1)$$

in which:
- $I_s$ is the saturation current under inverse polarization,
- e is the charge on an electron,
- V=V$_{applied}$−V$_{bi}$, V$_{bi}$ being the internal potential, and
- n is the ideality factor of the diode (0<n<1 in which 1 is the ideal case),
- k is the Boltzmann constant, and
- T is the temperature.

For an infinite potential, the ideality coefficient of the diode can be calculated according to the following equation $$n=(eV/kT)(\ln(R))^{-1}$$

in which R is the current ratio.

The current ratios (±1 V) and the shunt resistances obtained for the three devices are summarized in Table III.

TABLE III

| Device | Current ratio | Rshunt (in Ω · cm$^{-2}$) |
|---|---|---|
| Device 1 | 1.87 × 10³ | 2.5 × 10⁵ |
| Device 2 | 7.8 × 10³ | 1.43 × 10⁶ |
| Device 3 | 1.4 × 10² | 10⁵ |

The shunt resistance is the inverse of the slope of the characteristic current-voltage at the point of short-circuit (when V=0 V), and corresponds to the leakage currents present in the diode, these currents being associated with the presence of recombinations of charge carriers in the diode.

b) Characteristics Under Lighting

The characteristics under lighting are measured using an Oriel xenon lamp delivering a power of 75 mW·cm$^{-2}$ to the diode (under lighting). An AMG 1.5 (Air Mass Global 1.5) filter is placed between the lamp and the cell, this filter allowing the white light spectrum of the solar spectrum to be reproduced.

The results obtained are collated in the following table:

TABLE IV

| Device | Vmax (mV) | Imax (µA) | Isc (µA) | Shape factor (SF) | Phtotgenerated current Jsc (mA · cm$^{-2}$) |
|---|---|---|---|---|---|
| Device 1 | 260.7 | 502.5 | 801.76 | 0.3948 | 5.074 |
| Device 2 | 311.6 | 426.81 | 706.52 | 0.3677 | 4.07 |
| Device 3 | 443.3 | 308.06 | 524.23 | 0.3940 | 4.68 |

By drawing the characteristic current-voltage of a cell in the dark and under lighting, it is possible to evaluate the performance and the electrical behavior of the diodes. The following parameters may thus be defined (cf. FIG. 11):

the short-circuit current Isc obtained for a zero voltage. This current is proportional to the incident lighting (Jsc=Isc/S, where S is the active surface area of the electrode), the open-circuit voltage Voc measured for a zero current, Imax and Vmax are the coordinates I-V (Pmax=Imax×Vmax), represented by the dark gray rectangle in FIG. 11, the Shape Factor (SF) is equal to: SF=(Vmax×Imax)/(Voc×Isc)

I-V curves obtained for the three devices are shown in FIG. 12.

It is found that device 1 of the invention has better performances than those obtained for devices 2 and 3, and especially:

the photogenerated current Jsc is more than 20% greater than that measured for device 2 (greater than 1 mA·cm$^{-2}$ increase). This current is also greater than that obtained for device 3, which shows that the holes are collected more efficiently in the device of the invention, and the shape factor SF is also slightly higher for the device of the invention.

c) Experimental Determination of the Photocurrent

When a semiconductor is exposed to photons of energy higher than that of its optical gap, charge carriers are created. The existence of a potential intrinsic to the material or the application of an external potential may cause separation of the charges and produce a photocurrent in an external circuit.

Experimentally, the photocurrent is determined from the I-V response curves in the dark and under lighting, by virtue of the difference $(J_L-J_D)$, where $J_L$ is the current density obtained under lighting and $J_D$ is the current density obtained in the dark.

The change in the photocurrent $J_{ph}$ as a function of the potential effectively applied to the device $(V_o-V)$, wherein $V_o$ is the compensation potential determined on the I-V response curves in the dark (and which gives a direct measure of the intrinsic potential $V_{bi}$) and V is the potential applied to the electrodes, makes it possible to discriminate the regions in which the photocurrent is dominated by recombination phenomena (monomolecular or bimolecular), or by effects associated with a charge space regime, or by competitive effects between drift current and diffusion current.

The response curves for the photocurrent as a function of the effective potential in the device $(V_o-V)$ are shown in FIG. 13.

For values of $(V_o-V)$ of less than 0.1 V, a linear regime is observed for devices 2 and 3, and a slight deviation for the curve of device 1 of the invention. This phenomenon is explained by greater participation of the drift current relative to the diffusion current, for low voltages. For values of $(V_o-V)>0.1$ V, it is observed that the photocurrent follows a $V^{1/2}$ law, which is proof of the existence of a regime of SCLC (Space Charge Limited Current) type or of strong monomolecular recombinations. It should be noted that a regime of SCLC type is manifested when an accumulation of charges occurs at one of the electrodes of the device.

The dependence of the photocurrent on the incident light intensity is also determined. For chosen values of $(V_o-V)$, the values of the coefficients α of the power law $J=P^\alpha$ are characterized.

TABLE V

| Device | Coefficient α |
|---|---|
| Device 1 | 0.86 |
| Device 2 | 0.77 |
| Device 3 | 0.79 |

Devices 2 and 3 have coefficients close to 0.75. These values, which are close to the theoretical coefficient of a regime of SCLC type, suggest that the transport within the active layer of these devices is non-equilibrated and limited by the mobility of the holes of the active layer. The transport within devices 2 and 3 is thus limited by an accumulation of holes close to the anode interface.

In contrast, the value of the coefficient α determined for device 1 of the invention is higher and bears witness to a more equilibrated regime, which has an influence especially on the equilibrium of the charge transport of $P_3HT$. The substrate of the invention thus makes it possible to reduce the accumulation of charges at the electrode, by virtue of the numerous conduction paths observed and of the staged electronic levels between the substrate and the photosensitive active layer.

Influence of the Thickness and Morphology of the Films of the Invention on Non-Annealed Systems:

Three devices A, B and C comprising substrates coated with 2,2',6,6'-tetraphenyl-4,4'-dithiopyranylidene-based films and having different morphologies and thicknesses were evaluated.

TABLE VI

| Device | Evaporation regime of the films (Å/s) | Thickness of the layer (nm) |
|---|---|---|
| Device A | 0.1 | 18 |
| Device B | 0.1 | 45 |
| Device C | >2 | 37* |

*The thickness indicated for device C is an average since the film is non-uniform as a result of an unstable evaporation regime.

a) Characteristic in the Dark

The current ratios (±2 V) and the shunt and series resistances were determined, and are summarized in Table VII.

TABLE VII

| Device | Current ratio | Rshunt (Ω · cm$^{-2}$) | Rseries (Ω · cm$^{-2}$) |
|---|---|---|---|
| Device A | $1.2 \times 10^3$ | $2.5 \times 10^5$ | 277.8 |
| Device B | 90.9 | $5 \times 10^4$ | $3.33 \times 10^3$ |
| Device C | 126.4 | $3.33 \times 10^4$ | $2.5 \times 10^4$ |

The series resistances is the inverse of the slope of the characteristic current-voltage obtained for a voltage V greater than Voc.

The performance qualities of the diodes in the dark depend very significantly on the thicknesses and thickness morphologies of the films.

The most efficient diode is that which has the smallest thickness, the 2,2',6,6'-tetraphenyl-4,4'-dithiopyranylidene-based interface needing to be critical for excessive thicknesses.

The shunt resistance values observed for devices B and C are ten times smaller than that of device A. The series resistance values are, themselves, higher, which proves the reduction of the interfaces quality.

b) Characteristics Under Lighting

The various photovoltaic parameters obtained with AMG 1.5 lighting are collated in Table VIII below:

TABLE VIII

| Device | Vmax (mV) | Imax (μA) | Open-circuit voltage Voc (mV) | Isc (μA) | Shape factor (SF) | Photogenerated current Jsc (A·cm$^{-2}$) | Overall efficiency yield PCE (%) |
|---|---|---|---|---|---|---|---|
| Device A | 260.7 | 502.5 | 413.9 | 801.76 | 0.3948 | 5.074 | 1.11 |
| Device B | 133.7 | 202.43 | 251.1 | 379.45 | 0.2841 | 3.098 | 0.22 |
| Device C | 80.7 | 62.742 | 149.3 | 125.34 | 0.2706 | 1.066 | 0.06 |

The I-V response curves are shown in FIG. 14:

The curve corresponding to the heterogeneous film (device C) has an inverted shape factor (concave shape known as an "S-curve"). This S-shaped curve is generally associated with the presence of an interface of mediocre quality within the device, due to excessively rapid evaporation or to oxidation of the electrode. This inverted shape factor suggests that the interface is not optimized, since it can block the free charges collected at the ITO and slow down the charge transfer between the photosensitive active layer and the substrate of the invention.

The curve corresponding to the film 45 nm thick (device B) has a relatively small convex shape factor. Comparison of the curves for devices A and B suggests that part of the incident light is absorbed by the substrate of the invention, the number of photogenerated charges decreasing as the thickness of the film increases and explaining the small Voc and Jsc values obtained for device B (compared with device A).

The shunt and series resistances were also determined, and confirm the tendencies observed on the I-V curves (cf. Table IX):

TABLE IX

| Device | Rshunt (Ω·cm$^{-2}$) | Rseries (Ω·cm$^{-2}$) |
|---|---|---|
| Device A | 232 | 26.38 |
| Device B | 137 | 59.9 |
| Device C | 83.3 | 98.04 |

Compared Photovoltaic Properties of Devices 1, 2 and 3 with Annealing of the Active Layer:

The devices studied correspond to devices 1, 2 and 3 described previously, the only difference being the annealing of the photosensitive active layer.

The PEDOT-PSS layer is 20 nm and the thickness of the film of the invention is 14 nm.

The annealing was performed before evaporating the lithium fluoride (LiF) and the aluminum, by heating the devices in a tubular oven at a temperature of 110° C. during 10 minutes, under an inert atmosphere of argon.

It should be noted that the substrate of the invention is totally insensitive to such a heating temperature (since the melting point of 2,2',6,6'-tetraphenyl-4,4'-dithiopyranylidene is 328° C.), no modification of the surface of the substrate of the invention having been observed by AFM in current-sensing mode (no change in the occupation of the surface by the 2,2',6,6'-tetraphenyl-4,4'-dithiopyranylidene, or in its polycrystalline nature, and no variation in the size of the particles or in the roughness).

a) Characteristics in the Dark

The current ratios (±2 V) and the shunt and series resistances were determined and are summarized in Table X.

TABLE X

| Device | Current ratio | Rshunt (Ω·cm$^{-2}$) | Rseries (Ω·cm$^{-2}$) |
|---|---|---|---|
| Device 1 | 93.8 | 1.7 × 10$^4$ | 14.5 |
| Device 2 | 373 | 5 × 10$^4$ | 101.1 |
| Device 3 | 29.4 | 1 × 10$^4$ | 29.9 |

The series and shunt resistance values obtained are approximately of the same order of magnitude for the three devices. The series resistance values obtained show that the substrates of the invention (device 1) form interface layers of better quality than those of devices 2 and 3.

b) Characteristics Under Lighting

The various photovoltaic parameters obtained with AMG 1.5 lighting are collated in Table XI below:

TABLE XI

| Device | Vmax (mV) | Imax (μA) | Isc (μA) | Shape Factor (SF) | Photo-generated current Jsc (A·cm$^{-2}$) | Overall efficiency yield PCE (%) |
|---|---|---|---|---|---|---|
| Device 1 | 304.7 | 189.2 | 293.6 | 0.40 | 7.73 | 2.02 |
| Device 2 | 300.7 | 594.45 | 979.44 | 0.32 | 6.996 | 1.73 |
| Device 3 | 455.8 | 63.4 | 93.1 | 0.49 | 8.46 | 3.52 |

The I-V response curves are shown in FIG. 15.

A general improvement of the photovoltaic performance qualities after annealing is observed for the device using an anode interface layer according to the invention. The shape factor of device 1 is high and between that of the reference devices 2 and 3. The current density of device 1 is also between that of devices 2 and 3.

c) Experimental Determination of the Photocurrent

In order to differentiate the recombination processes participating in the generation of the photocurrent, the dependency of the photocurrent on the incident light intensity was studied. As previously, the values of the coefficients α of the power law J=P$^α$ were determined for selected (V$_o$-V) values.

TABLE XII

| Device | Coefficient α |
|---|---|
| Device 1 | 0.87 |
| Device 2 | 0.84 |
| Device 3 | 0.84 |

It is observed that the coefficients α are all of the same order of magnitude. By virtue of annealing of the active layer, the mobilities of the free charges are equilibrated in the bulk of the material, which improves the charge network in the material and reduces the large accumulation of holes close to the anode interface.

The power coefficient of the layer of the invention (device 1) is higher than that of devices 2 and 3, thus demonstrating the influence of the 2,2',6,6'-tetraphenyl-4,4'-dithiopyranylidene-based interface layer: the probabilities of recombination of the associated charges are lowered, the holes being collected more at the anode.

Photovoltaic Properties of a "Hybrid" Device and of Reference Systems, without Annealing of the Active Layer:

This study is based on three types of device bearing "hybrid" anode interface layers, the object of which study is to determine the parameters that influence the open-circuit voltage Voc.

To this end, three different devices were studied:

a device X ("hybrid" device) comprising an ITO substrate coated with a first uniform layer of 2,2',6,6'-tetraphenyl-4,4'-dithiopyranylidene 15 nm thick, itself coated with a layer of PEDOT-PSS 5 nm thick, and then with a photosensitive active layer, a device Y comprising an ITO substrate coated with a layer of PEDOT-PSS 5 nm thick, and then with a photosensitive active layer, a device Z comprising an ITO substrate coated solely with a photosensitive active layer.

The photosensitive active layers are made of $P_3HT$-PCBM and were prepared as described previously in the "Manufacture of the reference OSC devices" section. The active layers were not subjected to annealing.

Characterization by current-sensing AFM of the various devices made it possible to demonstrate a marked change in coverage by means of the 2,2',6,6'-tetraphenyl-4,4'-dithiopyranylidene-based film (cf. FIG. 16). The participation of the 2,2',6,6'-tetraphenyl-4,4'-dithiopyranylidene particles on the morphology of the fibrillar network of the "hybrid" layer is clearly distinguished in these images.

a) Characteristics in the Dark

The current ratios (±2 V) and the shunt and series resistances were determined and are summarized in Table XIII.

TABLE XIII

| Device | Current ratio | Rshunt (Ω · cm$^{-2}$) | Rseries (Ω · cm$^{-2}$) |
|---|---|---|---|
| Device X | 795 | 2.5 × 10$^5$ | 36.9 |
| Device Y | 34.9 | 5 × 10$^3$ | 117.6 |
| Device Z | 7.8 × 10$^3$ | 1.43 × 10$^6$ | 294.1 |

The recombination phenomena are less pronounced for the device of the invention, which proves of a network of good quality.

It is also noted that the interface formed solely from 2,2',6,6'-tetraphenyl-4,4'-dithiopyranylidene is of better quality than those of devices X, Y and Z (cf. previous results).

b) Characteristics Under Lighting

The various photovoltaic parameters obtained with AMG 1.5 lighting are collated in Table XIV below:

TABLE XIV

| Device | Vmax (mV) | Imax (μA) | Voc (mV) | Isc (μA) | Shape factor (SF) | Photogenerated current Jsc (A · cm$^{-2}$) | Overall efficiency yield PCE (%) |
|---|---|---|---|---|---|---|---|
| Device A | 350.1 | 166.53 | 523 | 2 63.58 | 0.423 | 5.23 | 1.54 |
| Device B | 362.1 | 374.75 | 591.2 | 591.82 | 0.39 | 4.065 | 1.24 |
| Device C | 311.6 | 426.81 | 511.9 | 706.52 | 0.3677 | 4.07 | 1.02 |

It is observed that the "hybrid" device made of 2,2',6,6'-tetraphenyl-4,4'-dithiopyranylidene and PEDOT-PSS is the most efficient of the three systems.

c) Experimental Determination of the Photocurrent

As previously, the values of the coefficients α of the power law $J=P^\alpha$ were determined for selected ($V_o-V$) values.

TABLE XV

| Device | Coefficient α |
|---|---|
| Device X | 0.88 |
| Device Y | 0.78 |
| Device Z | 0.77 |

The reference devices predominantly follow a charge accumulation regime of SCLC type (coefficients close to 0.75), in contrast with the device of the invention. Since the charge recombinations are low, these carriers are efficiently harvested at the electrodes.

The "hybrid" interface layer comprising 2,2',6,6'-tetraphenyl-4,4'-dithiopyranylidene participates in the collection of holes via its high intrinsic hole mobility, the conduction paths of the hybrid layer being attributable to the presence of the compound of formula (I) of the invention.

Photovoltaic Properties of a "Hybrid" Device and of Reference Systems with Annealing of the Active Layer:

This study is based on the three previous devices, the only difference being the annealing of the photosensitive active layer. These three devices are named X', Y' and Z' by analogy with devices X, Y and Z.

a) Characteristics in the Dark

The shunt and series resistances were determined, and are summarized in Table XVI.

TABLE XVI

| Device | Rshunt (Ω · cm$^{-2}$) | Rseries (Ω · cm$^{-2}$) |
|---|---|---|
| Device X' | 1 × 10$^5$ | 172.4 |
| Device Y' | 1 × 10$^4$ | 29.9 |
| Device Z' | 5 × 10$^4$ | 101.1 |

The characteristics of the diodes are virtually identical in the dark.

b) Characteristics Under Lighting

The various photovoltaic parameters obtained with AMG 1.5 lighting are collated in Table XVII below:

TABLE XVII

| Device | Vmax (mV) | Imax (µA) | Voc (mV) | Isc (µA) | Shape factor (SF) | Photogenerated current Jsc (A · cm$^{-2}$) | Overall efficiency yield PCE (%) |
|---|---|---|---|---|---|---|---|
| Device X' | 381.3 | 636.47 | 601.6 | 992.82 | 0.41 | 8.864 | 2.89 |
| Device Y' | 455.8 | 63.34 | 637.6 | 93.05 | 0.49 | 8.46 | 3.5 |
| Device Z' | 300.7 | 594.45 | 580 | 979.44 | 0.32 | 6.99 | 1.7 |

An improvement in the performance qualities following annealing of the photosensitive active layer is observed for the device bearing a "hybrid" interface.

The short-circuit current density of device X' is higher than those of the reference devices Y' and Z', which is explained by a favorable participation of the layer made of 2,2',6,6'-tetraphenyl-4,4'-dithiopyranylidene (energy barrier lowered at the interface of the "hybrid" layer and of the photosensitive active layer, which promotes charge transfer).

c) Experimental Determination of the Photocurrent

As previously, the values of the coefficients α of the power law J=P$^α$ were determined for selected (V$_o$–V) values.

TABLE XVIII

| Device | Coefficient α |
|---|---|
| Device X' | 0.93 |
| Device Y' | 0.84 |
| Device Z' | 0.84 |

The evolution of the coefficients α with annealing follows the evolution of the coefficients α obtained without annealing. The very high coefficient α obtained for the "hybrid" device X' corresponds to a combined effect of the reduction of dissociations of geminal pairs of excitons, and also to a reduction of the dissociated charges.

The invention claimed is:

1. A substrate, characterized in that it is coated with a film comprising at least one compound of formula (I) below:

(I)

in which:
Xa and Xb, which may be identical or different, are chosen from N, P, O, S, Se and Te atoms,
R$_1$, R$_2$, R$_3$ and R$_4$, which may be identical or different, represent a group chosen from aryl and heteroaryl rings containing 4 to 10 carbon atoms, said aryl or heteroaryl rings possibly being substituted with one or more halogen atoms, hydroxyl groups —OH, alkyls containing 1 to 30 carbon atoms, alkoxy —OC$_n$H$_{2n+1}$ or ester —C(O)OC$_n$H$_{2n+1}$, in which 0≦n≦16, the compound of formula (I) being present in said film in the form of spherical-like particles with a diameter of less than or equal to 300 nm.

2. The substrate as claimed in claim 1, characterized in that the atoms Xa and Xb of the compound of formula (I) are identical and chosen from O, S and Se atoms.

3. The substrate as claimed in claim 2, characterized in that Xa=Xb=S.

4. The substrate as claimed in claim 1, characterized in that the aryl or heteroaryl rings R$_1$, R$_2$, R$_3$ and R$_4$ of the compound of formula (I) are chosen from phenyl, naphthyl, anthracyl, benzoxazolyl, thiophenyl or alkoxythiophenyl, furyl, pyrrolyl, pyridyl, pyrazyl, pyrazolyl, pyridazyl, pyrimidyl, triazyl, imidazolyl, oxazolyl, indyl, indazolyl, quinolyl and quinoxalyl rings.

5. The substrate as claimed in claim 4, characterized in that the aryl or heteroaryl rings R$_1$, R$_2$, R$_3$ and R$_4$ of the compound of formula (I) are identical and chosen from the following phenyl, naphthyl or alkoxythiophenyl rings:

6. The substrate as claimed in claim 1, characterized in that it is coated with a film comprising at least one compound of formula (I) chosen from the following compounds:

Compound (1):

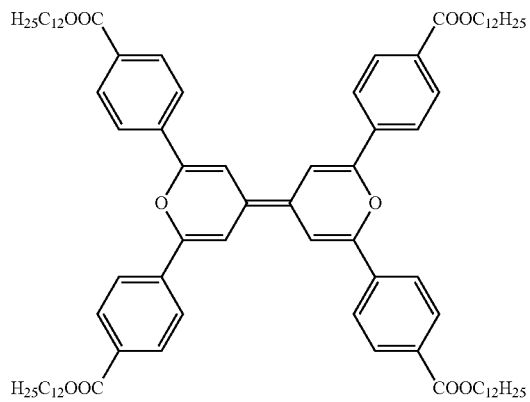

Compound (2):

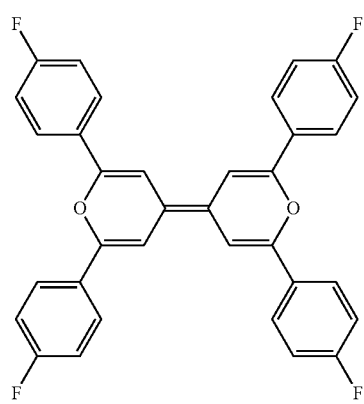

Compound (3):

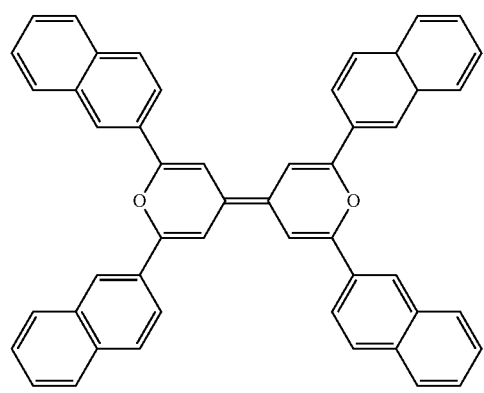

Compound (4):

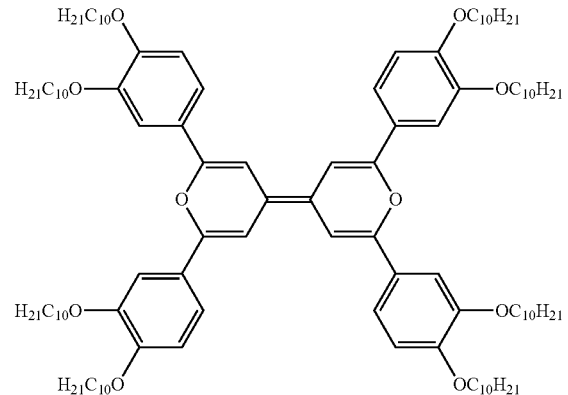

Compound (5):

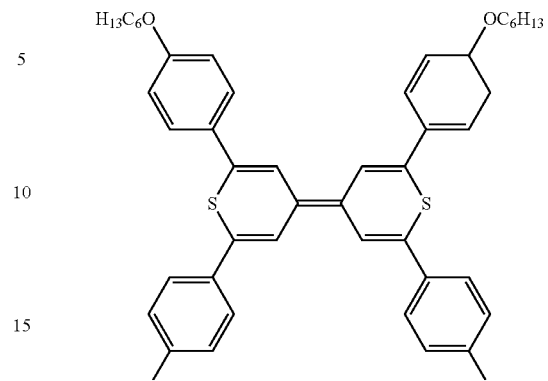

Compound (6):

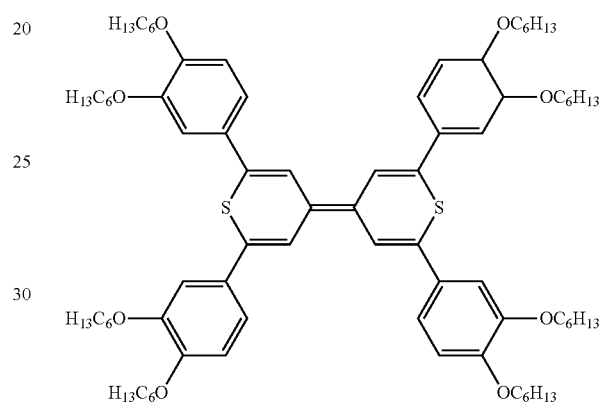

Compound (7):

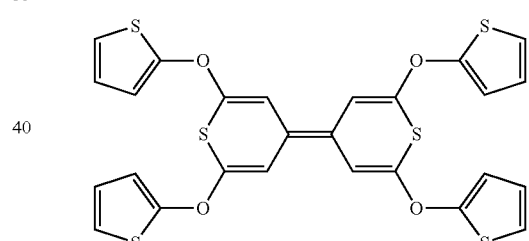

Compound (8):

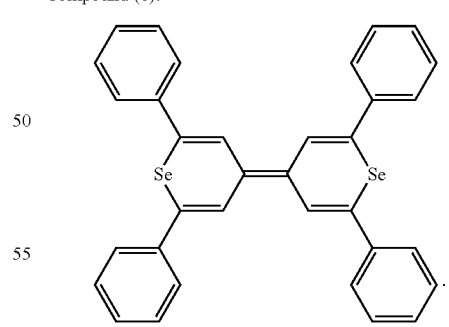

7. The substrate as claimed in claim 1, characterized in that said film has a thickness of less than 45 nm.

8. The substrate as claimed in claim 1, characterized in that it is made of tin-doped indium oxide (ITO), iron oxide, aluminum oxide or silicon oxide.

9. A process for manufacturing a substrate as defined in claim 1 characterized in that it comprises at least one step of dry-route deposition of a film comprising a compound of formula (I) as defined in claim 1, said deposition being performed at an evaporation rate of less than 1 Å/s.

10. The process as claimed in claim 9, characterized in that the dry-route deposition is performed by chemical vapor deposition CVD.

11. The process as claimed in claim 1, characterized in that the dry-route deposition is performed at an annealing temperature of between 80 and 120° C. and at a pressure of between $10^{-4}$ and $10^{-8}$ mbar, for a time of between 2 and 4 hours.

12. The substrate as claimed in claim 1, wherein the substrate comprises an anode interface layer in an electronic devices selected from the group consisting of organic electroluminescent diodes (OLED), polymeric electroluminescent diodes (PLED), organic field-effect transistors (OFET) and organic solar cells (OSC).

13. The substrate as claimed in claim 12, characterized in that the anode interface layer is a hole-collecting layer.

14. A finished article chosen from organic electroluminescent diodes (OLED), polymeric electroluminescent diodes (PLED), organic field-effect transistors (OFET) and organic solar cells (OSC), characterized in that it comprises at least one substrate as defined in claim 1.

15. An organic solar cell (OSC) as claimed in claim 14, characterized in that said substrate is made of tin-doped indium oxide (ITO).

16. The organic solar cell (OSC) as claimed in claim 14, characterized in that it comprises at least one base support (a) coated with said at least one substrate (b), said substrate itself being coated with a photosensitive active layer (c).

17. The organic solar cell (OSC) as claimed in claim 16, characterized in that the base support (a) is made of glass, the substrate (b) is made of tin-doped indium oxide (ITO) and the photosensitive active layer (c) is made of $P_3HT:PCBM$ (poly (3-hexylthiophene:methyl[6,6]phenyl-$C_{61}$-butyrate).

18. The organic solar cell (OSC) as claimed in claim 17, characterized in that the photosensitive active layer (c) is coated with a layer (d) made of lithium fluoride (LiF), and said layer (d) is itself coated with an electrolytic layer (e) made of aluminum, gold, calcium, copper, samarium, platinum, palladium, chromium, cobalt or iridium.

19. The process for manufacturing an organic solar cell (OSC) as defined in claim 14, characterized in that it comprises at least the following steps:

(i) the deposition of said at least one substrate (b) onto a base support (a), then (ii) the deposition of a photosensitive active layer (c), said deposition being performed using a spin coater, (iii) optionally, annealing of the photosensitive active layer (c) in a tubular oven, at a temperature of between 30 and 150° C., for a time of between 1 minute and 24 hours, under an inert atmosphere of argon, (iv) optionally, the deposition of a layer (d) made of lithium fluoride (LiF), said deposition being performed via a dry route, at an evaporation rate of less than 1 Å/s, (v) optionally, the deposition of an electrolytic layer (e), said deposition being performed via a dry route, at an evaporation rate of less than or equal to 3 Å/s.

20. A compound of formula (I) below:

Compound (1):

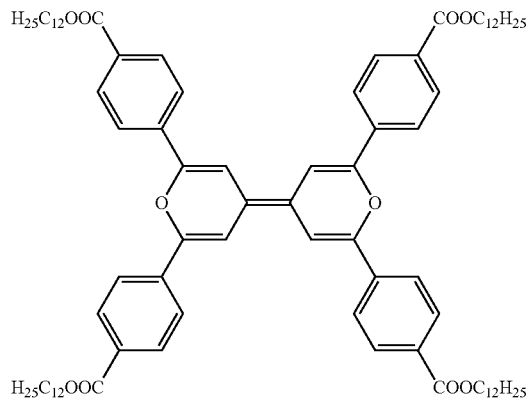

Compound (3):

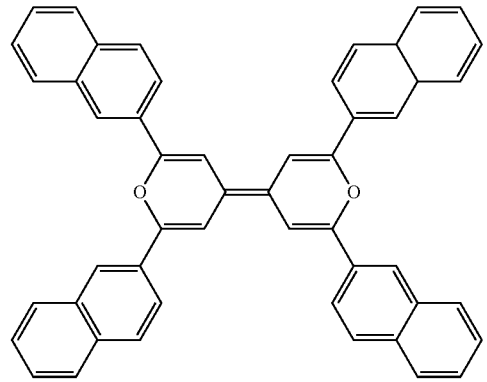

Compound (6):

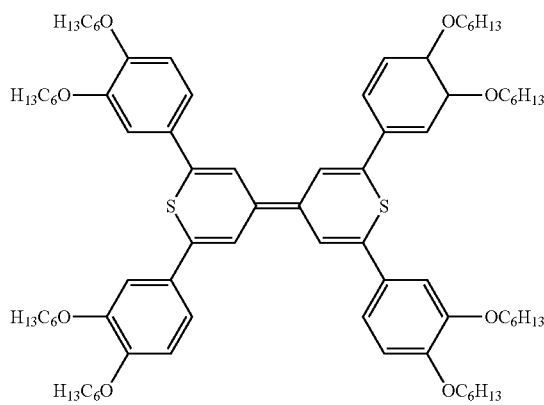

Compound (7):

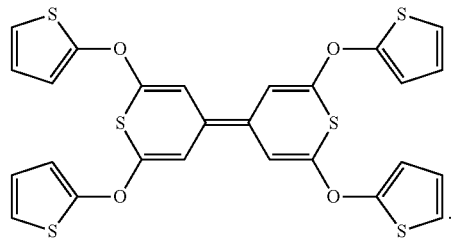

* * * * *

UNITED STATES PATENT AND TRADEMARK OFFICE
CERTIFICATE OF CORRECTION

PATENT NO. : 8,383,931 B2
APPLICATION NO. : 12/577945
DATED : February 26, 2013
INVENTOR(S) : Fichou et al.

It is certified that error appears in the above-identified patent and that said Letters Patent is hereby corrected as shown below:

In the Specifications

Column 18,
Line 53, the equation "n = (eV/kT)(1n(R))-1" should read --n = (eV/kT)(ln(R))-1--.

Signed and Sealed this
Twenty-eighth Day of May, 2013

Teresa Stanek Rea
*Acting Director of the United States Patent and Trademark Office*